US011904030B2

(12) United States Patent
Szillat et al.

(10) Patent No.: US 11,904,030 B2
(45) Date of Patent: Feb. 20, 2024

(54) DENTAL COMPOSITION

(71) Applicant: DENTSPLY DETREY GMBH, Constance (DE)

(72) Inventors: Florian Szillat, Constance (DE); Caroline Renn, Singen (DE); Christian Scheufler, Engen (DE); Jörg Brenneisen, Constance (DE)

(73) Assignee: DENTSPLY SIRONA INC., York, PA (US)

(*) Notice: Subject to any disclaimer, the term of this patent is extended or adjusted under 35 U.S.C. 154(b) by 595 days.

(21) Appl. No.: 16/977,905

(22) PCT Filed: Mar. 5, 2019

(86) PCT No.: PCT/EP2019/055393
§ 371 (c)(1),
(2) Date: Sep. 3, 2020

(87) PCT Pub. No.: WO2019/170640
PCT Pub. Date: Sep. 12, 2019

(65) Prior Publication Data
US 2020/0405585 A1 Dec. 31, 2020

(30) Foreign Application Priority Data
Mar. 7, 2018 (EP) ..................................... 18160500

(51) Int. Cl.
*A61K 6/61* (2020.01)
*A61K 6/889* (2020.01)
*A61K 6/898* (2020.01)

(52) U.S. Cl.
CPC ................ *A61K 6/61* (2020.01); *A61K 6/889* (2020.01); *A61K 6/898* (2020.01)

(58) Field of Classification Search
CPC ...................................................... A61K 6/61
See application file for complete search history.

(56) References Cited

U.S. PATENT DOCUMENTS

| 3,655,605 A | 4/1972 | Smith |
| 3,814,717 A | 6/1974 | Wilson |
| 4,143,018 A | 3/1979 | Crisp |
| 4,209,434 A | 6/1980 | Crisp |
| 4,298,738 A | 11/1981 | Lechtken |
| 4,324,744 A | 4/1982 | Lechtken |
| 4,360,605 A | 11/1982 | Schmitt |
| 4,376,835 A | 3/1983 | Schmitt |
| 4,385,109 A | 5/1983 | Lechtken |
| 4,814,362 A | 3/1989 | Billington |
| 5,154,762 A | 10/1992 | Mitra et al. |
| 5,318,929 A | 6/1994 | Jana |
| 5,357,012 A * | 10/1994 | Nussstein ............ C08F 251/00 526/238.2 |
| 5,360,770 A | 11/1994 | Chadwick |
| 5,382,571 A | 1/1995 | Granger et al. |
| 5,545,676 A | 8/1996 | Palazzotto |
| 6,180,739 B1 * | 1/2001 | Bowen ........................ C09J 4/00 526/238.2 |
| 2004/0079258 A1 | 4/2004 | Hoescheler |
| 2005/0165136 A1 | 7/2005 | Mays |
| 2006/0241205 A1 | 10/2006 | Jia |
| 2007/0072146 A1 | 3/2007 | Pierson |
| 2017/0296441 A1 | 10/2017 | Renn |

FOREIGN PATENT DOCUMENTS

| EP | 0173567 A2 | 3/1986 |
| EP | 0511635 A1 | 11/1992 |
| EP | 0969789 A2 | 1/2000 |
| EP | 2604247 A1 | 6/2013 |
| EP | 2705827 A1 | 3/2014 |
| EP | 2727576 A1 | 5/2014 |
| JP | H08500080 A | 1/1996 |
| JP | 2005248137 A | 9/2005 |
| JP | 2009509670 A | 3/2009 |
| WO | 9917716 A2 | 4/1999 |
| WO | 2016156363 A1 | 10/2016 |

OTHER PUBLICATIONS

Hyperbranched Polymers as Platforms for Catalysts; C. Hajji et al.; Topic in Organmetallic Chemistry, (2006), 20; pp. 149-176.
"Inclusion Complexation of the Sunscreen Agent 2-Ethylhexyl-p-dimethylaminobenzoate with Hydroxyproply-beta-cyclodextrin: Effect on Photostability"; Santo Scalia; J. Pharm. Pharmacol; Dec. 1, 1999; pp. 1367-1374; XP055508367.
P.G.M. Wuts and T.W. Greene; Greene's Protective Groups in Organic Synthesis, 4th Edition, John Wiley and Sons Inc. 2007.
Glass Ionomer Cement Formulations: I. The Preparation of Novel Fluoroaluminosilicate Glasses High in Fluorine; Journal of Dental Research; Jun. 1979; pp. 1607-1619.
Chemistry of Silanes: Interfaces in dental Polymers and Composites; J.M. Antonucci; Journal of Research of the National Institute of Standards and Technology, 2005, vol. 110 No. 5, pp. 541-558.
"Design of new dental adhesive—Effect of a water-soluble sodium acylphosphine oxide with crown ether on adhesion to dental hard tissue"; Ikemura et al.; Dental Materials Journal, the Japanese Society for Dental Materials and Devices; JP, vol. 28 No. 3, Aug. 14, 2009; pp. 267-276 (DOI: 10.4012/DMJ.28.267).
"Biotechnological applications of cyclodextrins"; Singh et al.; Biotechnology Advances; Elsevier Publishing, Barking, GB; vol. 20 No. 5-6; Dec. 1, 2002; pp. 341-359 (DOI: 10.1016/S0734-9750(02)00020-4).

(Continued)

Primary Examiner — Michael F Pepitone
(74) Attorney, Agent, or Firm — DENTSPLY SIRONA INC.

(57) ABSTRACT

The present invention relates to a dental composition comprising a radically polymerizable compound, a redox initiator system comprising one or more clathrate compounds comprising a host molecule and one or more guest molecules, wherein the host molecule is selected from cyclodextrines, crown ethers, cucurbituriles and calixarenes and the one or more guest molecules are reducing agents, and an oxidizing agent. Furthermore, the present invention relates to a use of the redox initiator system in a dental composition.

11 Claims, 2 Drawing Sheets

(56) References Cited

OTHER PUBLICATIONS

European Office Action dated Oct. 5, 2021.
International Search Report; PCT/EP2019/055393; May 21, 2019 (completed); dated May 29, 2019.
Written Opinion of the International Searching Authority; PCT/EP2019/055393; May 21, 2019 (completed); dated May 29, 2019.
International Preliminary Report on Patentability; PCT/EP2019/055393; May 21, 2019 (completed); dated May 29, 2019.

* cited by examiner

DENTAL COMPOSITION

FIELD OF THE INVENTION

The present invention relates to a dental composition comprising a radically polymerizable compound, a redox initiator system comprising one or more clathrate compounds comprising a host molecule and one or more guest molecules, wherein the host molecule is selected from cyclodextrines, crown ethers, cucurbituriles and calixarenes and the one or more guest molecules are reducing agents. Furthermore, the present invention relates to a use of the redox initiator system in a dental composition.

By forming a clathrate compound, a liquid reducing agent can be transformed into a solid. This renders possible to add a liquid reducing agent to a part or pack of the dental composition comprising only solid components.

BACKGROUND OF THE INVENTION

Redox initiator systems for a dental composition are well-known and contain reducing agents as an essential component. Aromatic tertiary amines, phosphines and boranes are frequently used as reducing agents in dental compositions. A major challenge with dental composition is storage stability when redox initiator systems are used. A dental composition comprising a radically polymerizable compound and a redox initiator system is required to have sufficient storage stability in order to be useful in practice. On the other hand, the dental composition must have a low kinetic stabilty allowing efficient activation while still providing a sufficient working time. Following the working time, the reactivity of the dental composition must be high enough to fully cure the dental composition in a short setting time. An increase of the thermodynamic stability of a dental composition usually leads to an increase of the kinetic stability and a reduced reactivity whereby storage stability may be increased. However, activation of the dental composition becomes more difficult whereby the setting time may deteriorate. On the other hand, a decrease of the thermodynamic and kinetic stability of a dental composition may lead to a deterioration of the storage stability of the dental composition or a component of the redox initiator system.

US-A 2005/165136 discloses a two-component (liquid and solid) redox initiator containing hybrid glass-ionomer cement. The liquid component containing an oxidizer was prepared by mixing a vinyl containing terpolymer (40-60% of total liquid, wt %) with $K_2S_2O_6$ (0.1-0.5%), butylated hydroxytoluene (BHT, 0.2-0.8%), polyoxyethylene nonylphenol (PEONP, 0.6%), vinyl-containing amino acid (20-30%) and distilled water (15-30%). The solid component containing a reducing agent was prepared by mixing GC FujiII LO glass powder (GC American Dental Co.) with ascorbic acid containing microcapsules (32-0.6% of glass powder, wt %), using a vortex with a maximal speed. A powder/liquid ratio (P/L) of 1.0-2.5/1 was used in the formulation. US-A 2005/165136 does not disclose molecular host-guest complexes having defined properties which are different from the compounds forming the host guest complexes. Rather, US-A 2005/165136 is limited to macroscopic coatings for reactive substances, which provide compositions having properties which are difficult to control.

EP 0 511 635 A1 discloses a multicomponent adhesive composition for aerospace and automotive uses, containing a polymer starter, a starter stabilizing agent, an elastomer dissolved in a polymerizable acrylic component, and a starter-activating agent. The polymer starter may be a peroxide compound complexed with a cyclodextrin as the starter stabilizing agent. It was found that by housing the peroxide compound in the cavity of the starter-stabilizing agent, thermal decomposition of the starter can be prevented, without altering its capability of starting the polymerization within the adhesive system.

Furthermore, it is known that amines and phosphines may form clathrate compounds.

C. Hajji et al., Topics in Organometallic Chemistry, 2006, 20, 149-176, page 169 discloses clathrates formed of phosphines and host molecules.

J. Mohanty et al., Comprehensive Supramolecular Chemistry II vol. 1, 2017, page 439 discloses clathrates formed of amines and host molecules.

SUMMARY OF THE INVENTION

It is an object of the present invention to provide a dental composition comprising a radically polymerizable compound and a redox initiator system, which provides at the same time excellent storage stability as well as a sufficiently longworking time and a short setting time.

According to a first aspect, the present invention provides a dental composition comprising
  (i) a radically polymerizable compound; and
  (ii) a redox initiator system comprising
    (a) one or more clathrate compounds comprising
      (a1) a host molecule and
      (a2) one or more guest molecules, wherein the host molecule is selected from cyclodextrines, crown ethers, cucurbituriles and calixarenes, and the one or more guest molecules are reducing agents; and
    (b) an oxidizing agent.

According to a second aspect, the present invention provides a use of a redox initiator system comprising
  (a) one or more clathrate compounds comprising a host molecule and one or more guest molecules, wherein the host molecule is selected from cyclodextrines, crown ethers, cucurbituriles and calixarenes, and the one or more guest molecules are reducing agents; and
  (b) an oxidizing agent,
in a dental composition, in particular a dental composition according to the first aspect of the present invention.

According to a third aspect, the present invention provides a container for storing a dental composition, which comprises a dental composition according to the first aspect of the present invention.

The present invention is based on the recognition that a specific clathrate compound comprising (a1) a host molecule selected from cyclodextrines, crown ethers, cucurbituriles and calixarenes and (a2) one or more guest molecules being reducing agents, provides a combination of thermodynamic and kinetic stability in a dental composition comprising a radically polymerizable compound providing an advantageous working time and setting time of the dental composition, while the dental composition also has an excellent storage stability. Accordingly, by forming a clathrate compound, a liquid reducing agent can be transformed into a solid. This renders possible to add a liquid reducing agent to a part or pack of the dental composition comprising only solid components.

DETAILED DESCRIPTION OF PREFERRED EMBODIMENTS

Figure 1:
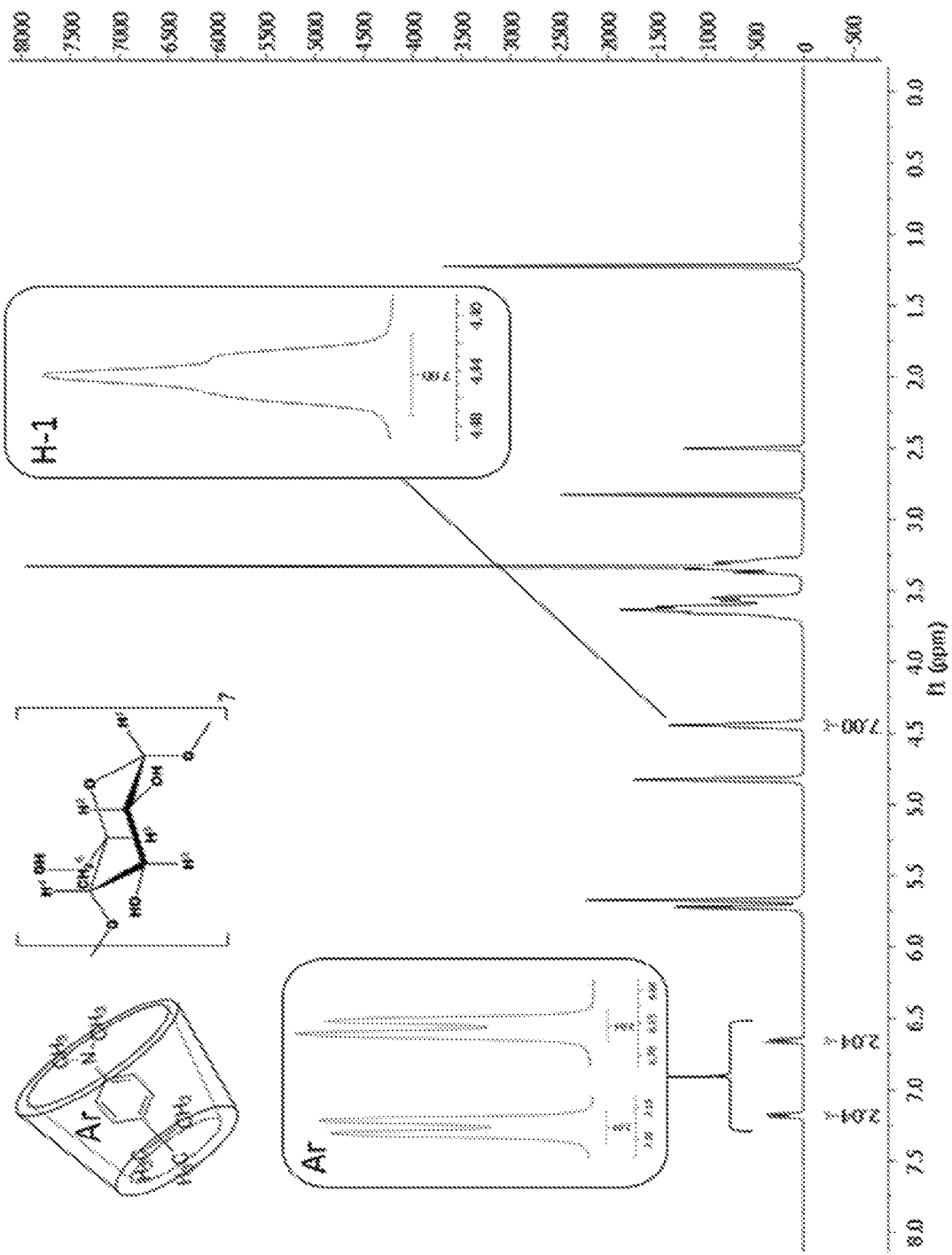
FIG. 1 shows $^1$H-NMR spectra of tBDA-clathrate in DMSO-d6. The stoichiometry of the complex formed was determined from the ratio of the peak areas for the aromatic protons of the tBDA (four protons) between 6.60-7.25 ppm and the H-1 glucoside protons (normalized on seven protons) of the β-Cyclodextrin at 4.45 ppm.

The terms "polymerization" and "polymerizabe" relate to the combining or the capability to combine by covalent bonding of a large number of compounds such as smaller molecules, for example monomers, to form larger molecules, that is, macromolecules or polymers. The polymerizable compounds may be combined to form only linear macromolecules or they may be combined to form three-dimensional macromolecules, commonly referred to as crosslinked polymers. For example, monofunctional polymerizable compounds form linear polymers, whereas polymerizable compounds having at least two functional groups form crosslinked polymers also known as polymer networks. In case of a higher conversion rate of the polymerizable compounds, the amount of multifunctional polymerizable compounds may be reduced or the leaching problem may be alleviated.

The term "radically polymerizable compound" as used herein means a compound having at least one radically polymerizable bond, preferably a carbon-carbon double bond The term "curing" means the polymerization of functional polymerizable compounds such as monomers, oligomers or even polymers, into a polymer network, preferably a cross-linked polymer network.

The term "redox initiator system" as used herein means a system comprising a combination of an oxidizing agent and a reducing agent, and optionally a catalyst such as a metal salt.

The redox initiator system provides for a redox reaction in which radicals are formed. These radicals initiate polymerisation of a radically polymerizable compound. Typically, a redox initiator system is activated, that is redox reaction is initiated, by bringing the redox initiator system in contact with water and/or an organic solvent providing for at least partial dissolution of the oxidizing agent and the reducing agent. The optional catalyst may be added to accelerate the redox reaction and thus the polymerization of the radically polymerizable compound.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration. In a setting reaction, due to the presence of polymerizable double bonds, a polymerization reaction takes place.

In addition to the polymerization reaction, in a glass ionomer cement, the setting reaction additionally involves neutralization of acid groups, for example of polymerizable compounds, by a base in the form of a reactive particulate glass.

The term "storage stability" as used herein means that the dental composition keeps its characteristics, in particular its working time and setting time, even after a long storage time of for example about 2 years.

The term "clathrate compound(s)" as used herein means inclusion compounds in which the "guest molecule" is in a cage formed by the "host molecule" or by a lattice of host molecules.

The term "peroxides" as used herein means compounds of the formula $R_x$—O—O—$R_y$ in which $R_x$ and $R_y$ independently from each other denote any suitable organic or inorganic group. For example, "organic peroxides" may include peroxyesters, such as tert-butyiperoxybenzoate, in which one organic group $R_x$ or $R_y$ is an acyl group. An acyl group is an organic group having a carbonyl group (—(C=O)—) to which, in the present case, the peroxo moiety (—O—O—) is bound. Furthermore, "organic peroxides" may also include diacylperoxides, such as benzoyl peroxide, in which both organic residues $R_x$ and $R_y$ represent acyl groups, dialkylperoxides, such as as di-tert-butyl peroxide, in which both organic residues $R_x$ and $R_y$ are alkyl residues, and peroxydicarbonates, such as diisopropyl peroxydicarbonate, in which both organic residues $R_x$ and $R_y$ represent carbonyloxyaikyi groups. For example, "inorganic peroxides" may include potassium persulfate or potassium peroxidisulfate.

The term "hydroperoxides" as used herein means compounds of formula $R_x$—O—O—H in which $R_x$ denotes any organic group. For example, "organic hydroperoxides" may include peroxy acids, such as peroxybenzoic acid, in which the organic group $R_x$ is an acyl group.

The term "cyclodextrins" as used herein means cyclic oligoglucosides, which cycle conventionally contains 5 to 10 glucose residues, or derivatives of cyclodextrins. In derivatives of cyclodextrins, typically, free hydroxyl groups of the cyclodextrin are suitable derivatised, e.g. by etherification or esterification. Examples for derivates of cyclodextrins are (meth)acrylated, alkylated, hydroxyalkylated or sulfoalkylated cyclodextrins. In cyclodextrins, typically, the glucose residues are linked by an α-1,4 linkage. Depending on the number of glucose residues forming the cycle, the cyclodextrins are typically divided into the following types: α-cyclodextrins formed of 6 glucose residues, β-cyclodextrins formed of 7 glucose residues, γ-cyclodextrins formed of 8 glucose residues, and δ-formed of 9 glucose residues.

The term "crown ethers" as used herein means cyclic ethers having ethyleneoxy units (—$CH_2CH_2O$—). Their nomenclature "[m]-crown-n" is based on the number m of ring members and the number n of heteroatoms. For example, [12]-crown-4 is 1,4,7,10 tetraoxacyclododecane, [15]-crown-5 is 1,4,7,10,13-pentaoxacyclopentadecane, and [18]-crown-6 is 1,4,7,10,13,16-hexaoxacyclooctadecane. Crown ethers may not only consist of ethyleneoxy units. For example, instead of the ethylene unit of the ethyleneoxy unit, a unit with two bridging carbon atoms, such as 1,6-benzenediyl may be present, like in dibenzo-[18]-crown-6 being 11,12-dibenzo-1,4,7,10,13,16-hexaoxacyclooctadecane. Furthermore, instead of the oxygen atom of the ethyleneoxy unit, another heteroatom may be present, for example a nitrogen atom, like in diaza-[18]-crown-6 being 1,4,10,13-tetraoxa-7,16-diazacyclooctadecane.

The term "cucurbituril" as used herein means macrocycic molecules formed from tetrahydroimidazo[4,5-d]imidazole-2,5(1H,3H)-dione (glycoluril) monomers and formaldehyde by condensation reaction. Thereby, the nitrogen atoms of the units deriving from glycoluril are linked with methylene bridges and form the cucurbituril repeating units:

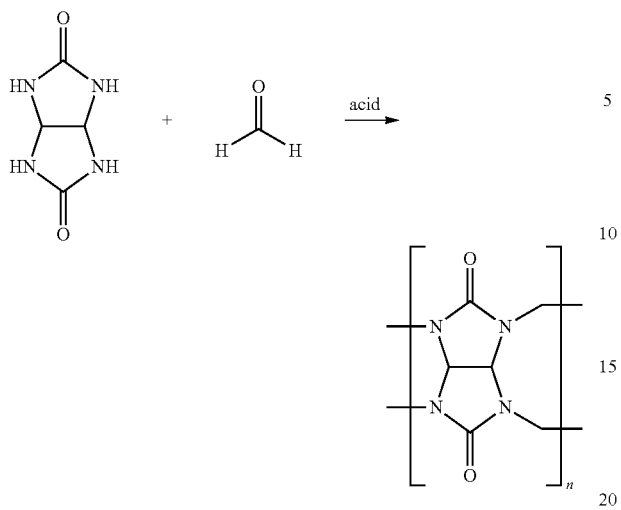

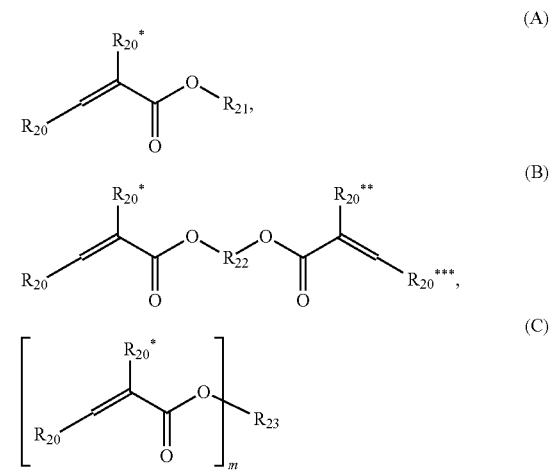

Typically, the cucurbiturils are termed "cucurbit[n]uril", or as abbreviations CB[n] or CBn, based on the number n of their repeating units. Typical and commercially available cucurbiturils are CB[5], CB[6], CB[7] and CB[8].

The term "polymerization accelerator" means any substance which is able to increase the reactivity of the redox initiator system whereby the polymerization accelerator is not complexed in by a host molecule Examples of the polymerization accelerator include sulfinic acids, sulfinates, sufites, hydrogen suflites, aldehydes, thiourea compounds, barbituric acid derivatives, triazine compounds, halogen compounds, and thiol compounds.

The present invention provides a dental composition being polymerizable or copolymerizable by a redox initiator system.

The dental composition may be a dental material to be used in the oral cavity. Preferably, the dental composition according to the invention is selected from a dental adhesive composition, a dental bonding agent, a dental primer, a dental infiltrant, a pit and fissure sealant, a dental desensitizing composition, a pulp capping composition, a dental composite, dental glass ionomer cement, a dental cement, a seal and protecting composition for naked tooth necks, and a dental root canal sealer composition.

The Radically Polymerizable Compound (i)

The dental composition of the present invention comprises (i) a radically polymerizable compound. The dental composition may comprise one or more radically polymerizable compounds (i).

The term "radically polymerizable compound" as used herein encompasses monomers, oligomers and polymers.

The radically polymerizable compound (i) is not particularly limited concerning its radically polymerizable groups. The radically polymerizable compound (i) may have one or more radically polymerizable groups. At least one radically polymerizable group may for example be a radically polymerizable carbon-carbon double bond, which may be selected from (meth)acryloyl group(s) and a (meth)acrylamide group(s), preferably (meth)acryloyl group(s).

Suitable examples for a radically polymerizable compound (i) in the form of a monomer may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

wherein $R_{20}$, $R^*_{20}$, $R^{}_{20}$, $R^{*}_{20}$ independently represent a hydrogen atom, —COOM, a linear $C_{1-18}$a or branched $C^{3-18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —PO$_3$M, —O—PO$_3$M$_2$ or —SO$_3$M*, $R_{21}$ represents a hydrogen atom, a linear $C_{1-18}$ or branched $C_{3-18}$ alkyl group or $C_2$ to $C_{18}$ alkenyl group which may be substituted by a $C_{3-6}$ cycoalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M*, or a $C_5$ to $C_{18}$; aryl or $C_3$ to $C_{18}$; heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C═O)—O— or —O—(C═O)—), 1 to 7 amide groups (—(C═O)—NH— or —NH—(C═O)—) or 1 to 7 urethane groups (—NH—(C═O)—O— or —O—(C═O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group, —COOM, —PO$_3$M, —O—PO$_3$M$_2$ or —SO$_3$M*; preferably $R_{22}$ is a $C_1$ to $C_{18}$ alkylene group or a $C_2$ to $C_{18}$ alkenylene group, which may be substituted by one or more —OH group(s), which alkylene or alkenylene group may contain at least one of 1 to 4 $C_{6-10}$ arylene groups, 1 to 4 urethane groups (—NH—(C═O)—O— or —O—(C═O)—NH—) and 1 to 8 oxygen atoms;

$R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkyaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, $R^{*}_{20}$, $R_{21}$, and $R_{22}$, which M are independent from each other, each represent a metal atom.

For $R_{20}$, $R^*_{20}$, $R^{}_{20}$ and $R^{*}_{20}$ the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the $C_{1-18}$ alkyl group or $C_{2-118}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, $R^{*}_{20}$ and $R_{21}$ an aryl group may, for example, be a phenyl group or a naphthyl group, and a $C_{3-14}$ heteroaryl group may contain 1 to 3 heteratoms selected from nitrogen, oxygen and sulfur.

For $R_{22}$, in the phrase "divalent organic residue may contain at least one of . . . " means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C=O)—O— or —O—(C=O)—NH—) are incorporated in the divalent organic residue of $R_{22}$.

In formula (B), the dotted bond indicates that $R_{20}$ and $R^{***}_{2D}$ may be in (Z) or (E) configuration relative to CO.

Preferably, in formulae (A), (B) and (C), $R_{20}$, $R^*_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^*_{20}$, $R^{}_{20}$ and $R^{*}_{20}$ independently represent a hydrogen atom, a linear $C_{1-8}$ or branched $C_{3-8}$ alky group which may be substituted by a $C_{4-6}$ s cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-6}$ heteroaryl group or a $C_{6-10}$ aryl group. Even more preferably, $R_{20}$, $R^*_{20}$, $R^{}_{20}$ and $R^{*}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^*_{20}$, $R^{}_{20}$, and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$, alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or $C_{3-6}$alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4)_(UDMA), glycerol mono- and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentyiglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryoxyethyl-dimethyicyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryoxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethy-2-methacryoxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methy-2-methacryloxyethyl-4-cyclohexyl carbamate, di-1-chloromethyl-2-methacryloxyethyl-hexamethylene dicarbamate, di-1-chloromethy-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryoxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryoxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Most preferably, a compound of formula (B) is selected from the group consisting of:

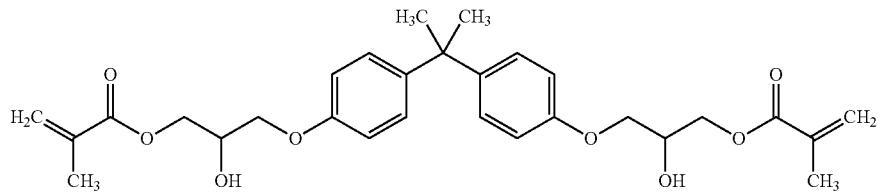

BisGMA

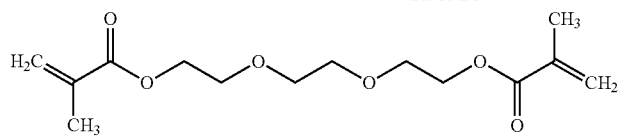

TEGDMA

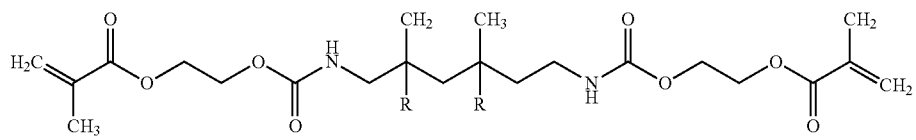

R = H or CH3(-1:1)
UDMA

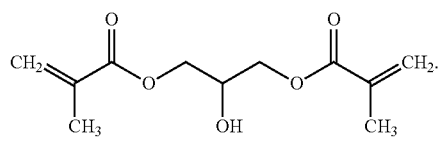

GDM

Particular preferred mono- or bis- or (meth)acrylamides and poly[(meth) acryamides] have the following formulae (D), (E) and (F):

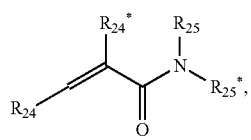
(D)

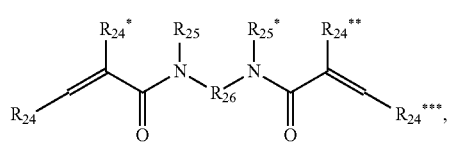
(E)

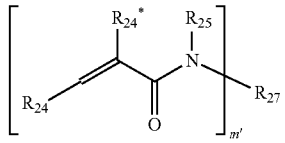
(F)

wherein $R_{24}$ $R^*_{24}$, $R^{}_{24}$, $R^{*}_{24}$ have the same meaning as $R_{20}$ $R^*_{20}$, $R^{}_{20}$, $R^{*}_{20}$ defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO$_3$M, —O—PO$_3$M$_2$ or —SO$_3$M* Preferably, $R_{26}$ is a $C_1$ to $C_{16}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

For $R_{26}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25}^*$ may cooperatively form a ring in which $R_{25}$ and $R_{25}^*$ are linked by a C—C bond or a functional group selected from the group consisting of an ether group, a thioether group, an amine group and an amide group.

Preferred methacrylamides according to formulae (D), (E), (F) have the following formulae:

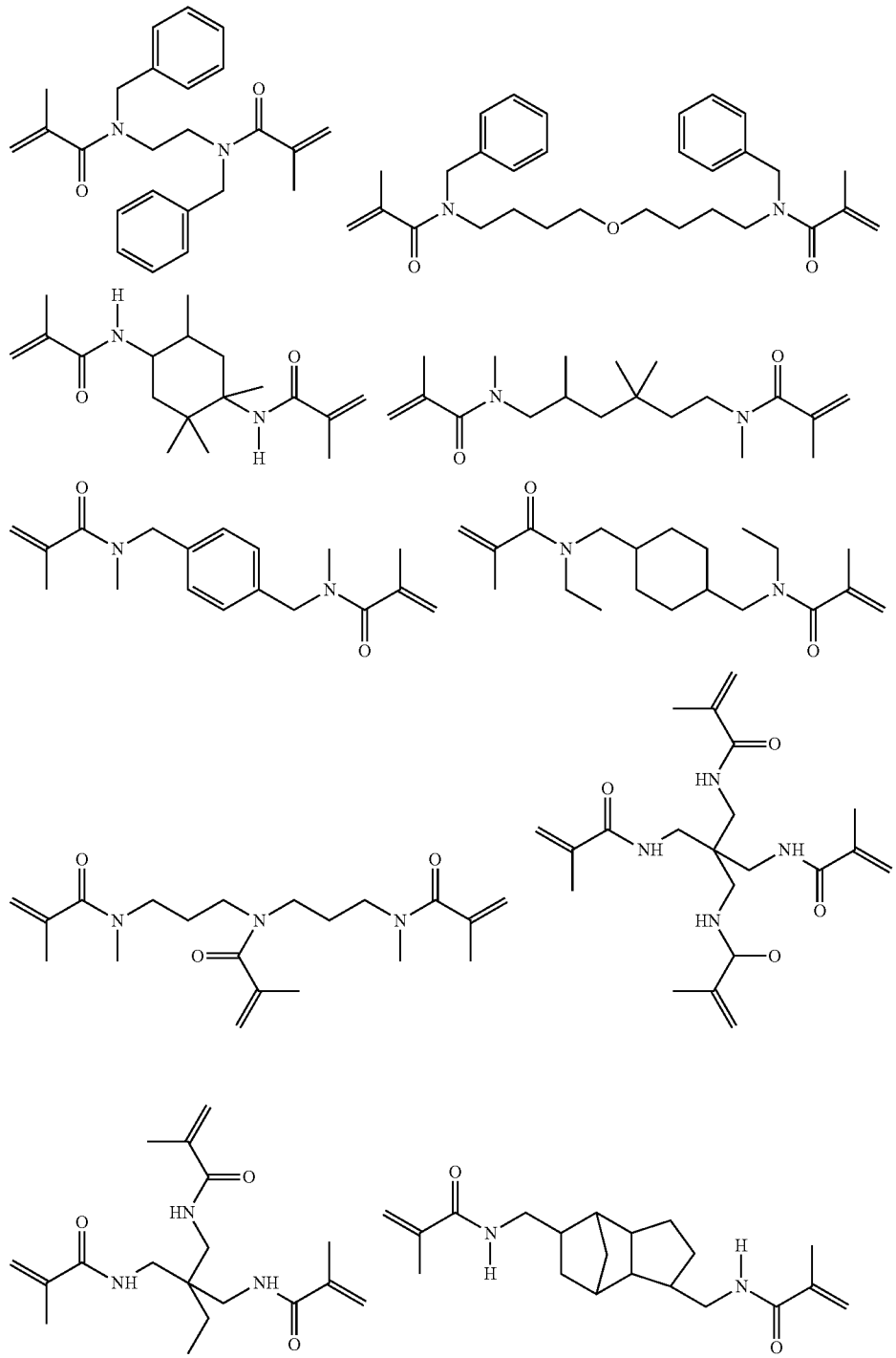

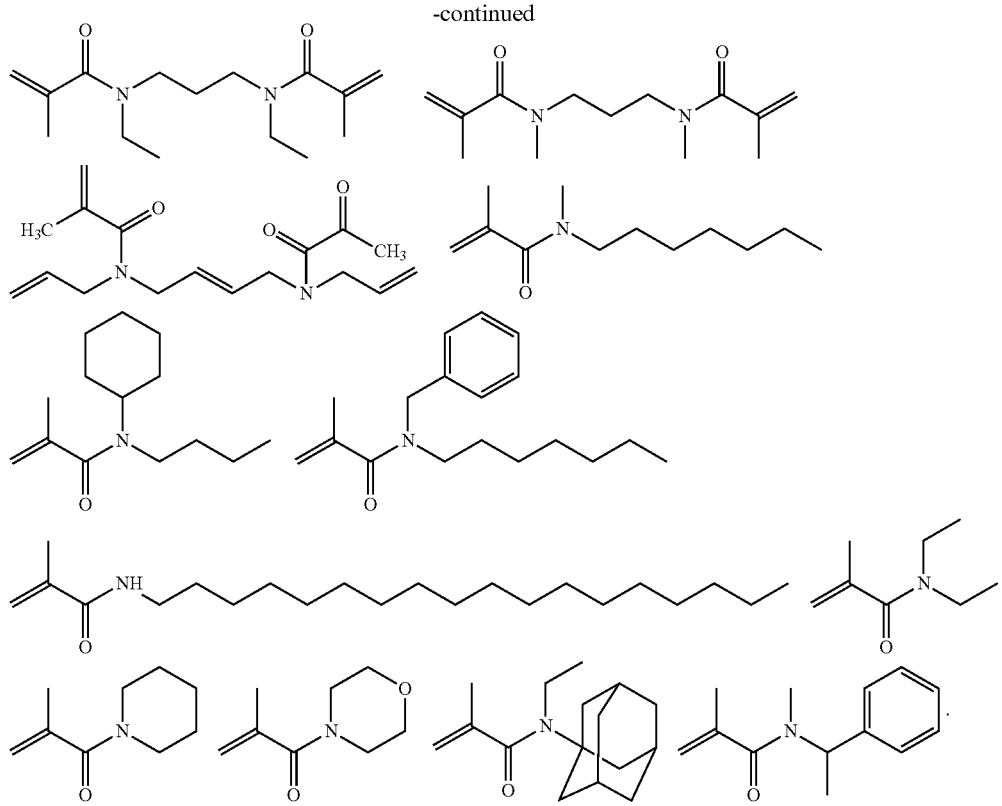
Preferred acrylamides according to formulae (D), (E), (F) have the following formulae:
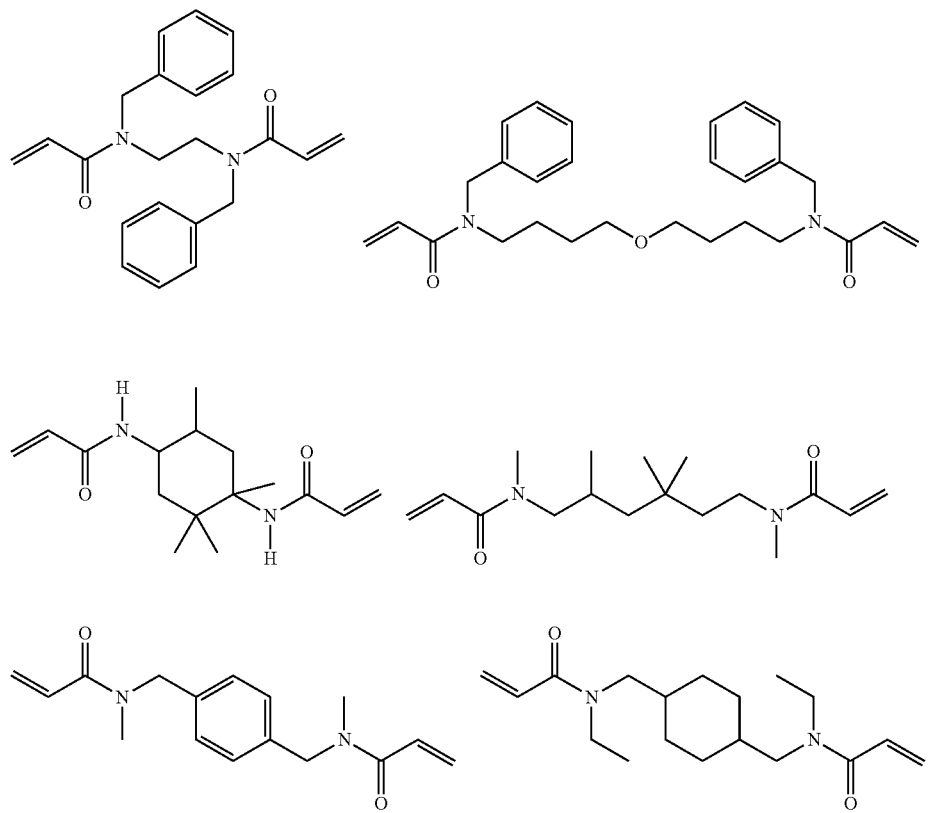

-continued
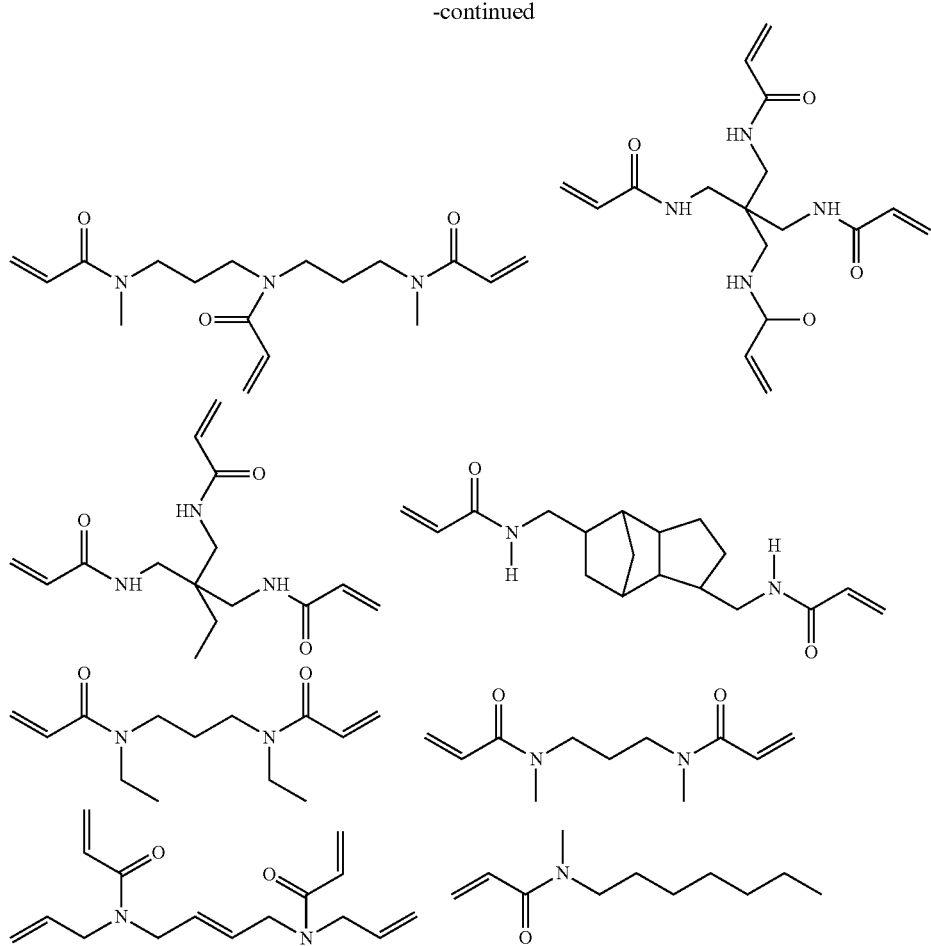
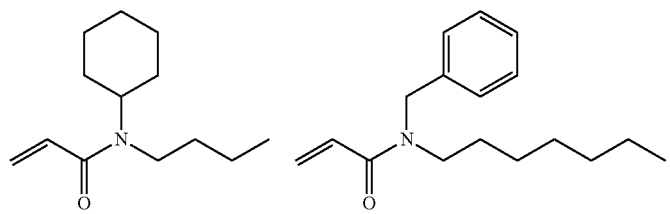
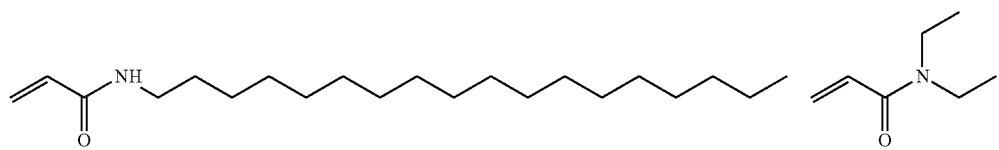
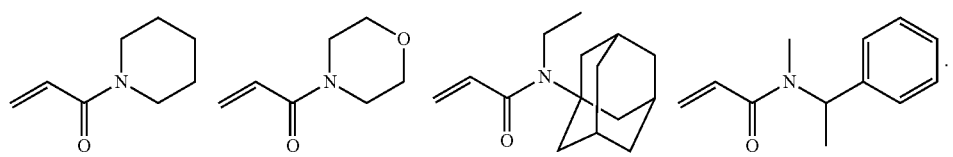

Most preferred are the bis-(meth)acrylamides:
N,N'-diallyl-1,4-bisacrylamido-(2E)-but-2-en (BAABE) having the structural formula

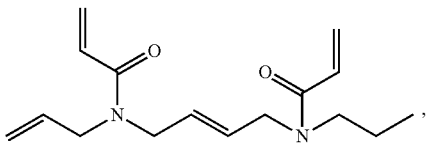 [SMILES: C=CCN(C/C=C/CN(CCC)C(=O)C=C)C(=O)C=C]

and
N,N'-diethyl-1,3-bisacrylamido-propan (BADEP) having the structural formula

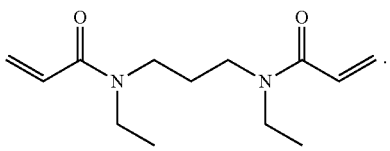 [SMILES: C=CC(=O)N(CC)CCCN(CC)C(=O)C=C]

A radically polymerizable compound (i) having a (meth.) acryloyl group or a (meth)acrylamide group may also be selected from phosphoric acid ester group containing polymerizable monomers having at least one radically polymerizable double bond. Preferably, such phosphoric acid ester group containing polymerizable monomers have the following formula (G):

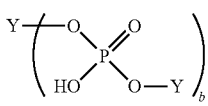
(G)

wherein
the moieties Y independent from each other represent a hydrogen atom or
a moiety of the following formulae (Y*), (Y) or (Y*):

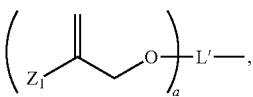
(Y*)

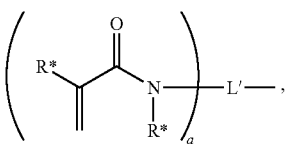
(Y**)

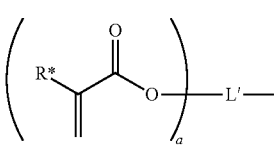
(Y***)

wherein
$Z_1$ is $COOR^\alpha$, $COSR^\beta$, $CON(R^\alpha)_2$, $CONR^\alpha R^\beta$, or $CONHR^\alpha$, wherein $R^\alpha$ and $R^\beta$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{13}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

R* and R* independently represent a hydrogen atom, an optionally substituted $C_{1-18}$ alkyl group, an optionally substituted $C_{3-18}$ cycoalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP 1 548 021 A1.

Furthermore, a radically polymerizable compound (i) having a (meth)acryloyl group or a (meth)acrylamide group may also be selected from phosphonic acid group containing polymerizable acidic compounds of the following formula (H):

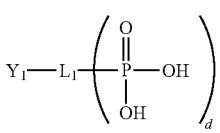
(H)

wherein
the moiety $Y_1$ represents a moiety of the following formulae ($Y_1$) or ($Y_1$*):

($Y_1$*)

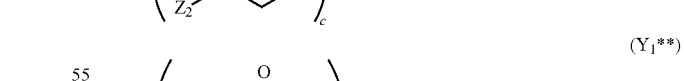
($Y_1$**)

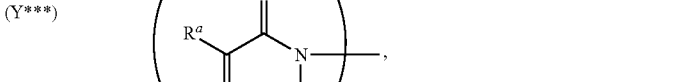
($Y_1$***)

$Z_2$ independently has the same meaning as defined for $Z_1$;
$R^\alpha$ and $R^\circ$ independently have the same meaning as defined for $R^*$ and $R^{**}$;
$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula $(Y_1^*)$, $(Y_1^{})$ and $(Y_1^{*})$; and
c and d independently represent integers of from 1 to 10.

From compound of formula (G'), the following formulae are particularly preferred:

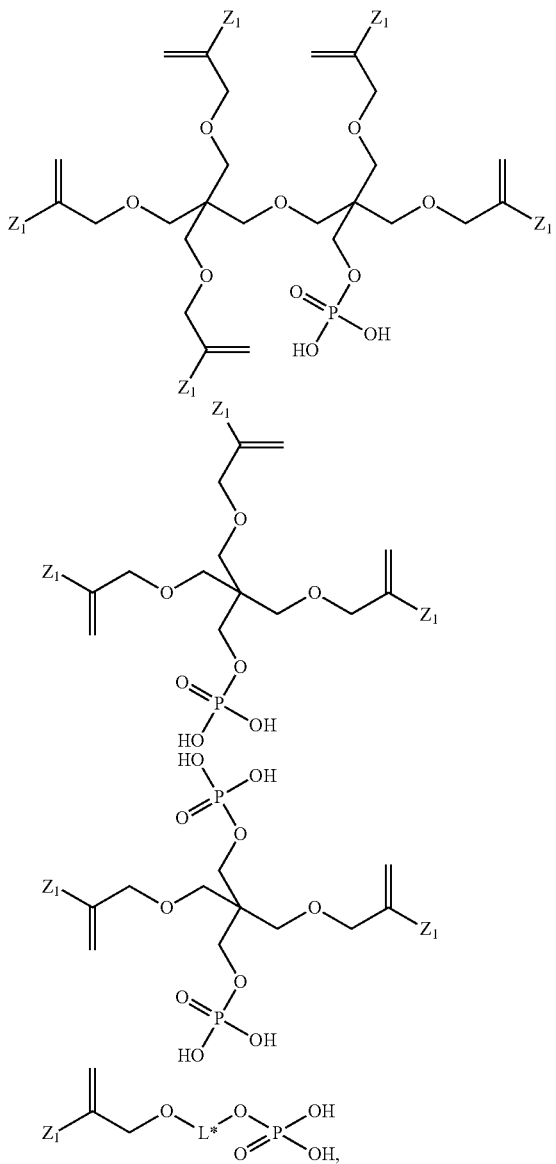

wherein $Z_1$ is defined as above, and L* is an optionally substituted alkylene group. More preferably $Z_1$ is methyl and L* is a $C_4$ to $C_{16}$ alkylene group. Even more preferably, L* is a $C_8$ to $C_{12}$ alkylene group.

Furthermore, a radically polymerizable compound (i) having one or more radically polymerizable carbon-carbon double bond(s) may be selected from the hydrolysis stable polyfunctional polymerizable monomers disclosed in EP 2 705 827 and EP 2 727 576.

Particularly preferred radically polymerizable compound(s) (i) are selected from the compounds of formulae (D), (E), (F), (G) and (H), more preferably from the compounds of formulae (D), (E), (F), and most preferably from compounds of formula (E).

Radically polymerizable compound(s) (i) in the form of polymers are preferably selected from polymerizable polyacidic polymers.

The term "polymerizable" as used with the term "polymerizable polyacidic polymer" means a polymer capable of combining by covalent bonding in an addition polymerization. The "polymerizable polyacidic polymer" may be combined with a crosslinker as well as e.g. with a monomer having polymerizable (carbon-carbon) double bond, to form graft polymers and/or crosslinked polymers when curing the dental composition.

The term "polyacidic" as used with the term "polymerizable polyacidic polymer" means that the polymer has a plurality of acidic groups, preferably carboxylic acid groups, which may participate in a cement reaction with a reactive glass. The carboxylic acid groups are preferably present in the backbone and derived from acrylic acid, methacrylic acid and/or itaconic acid. Additional acidity may be introduced by carboxylic acid groups in the group of formula (II) and carboxylic group(s) in the optional repeating unit of formula (III).

A particularly preferred radically polymerizable polyacidic polymer has repeating units of the following formula (I);

wherein $R^1$ represents a group of the following formula (II):

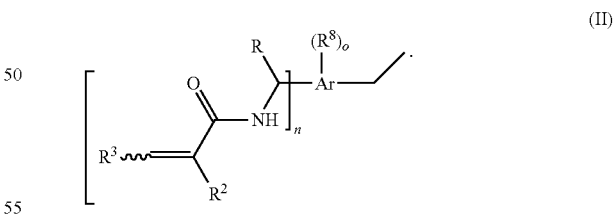

In formulae (II) and (VI), the jagged bond indicates that $R^3$ may be in cis or trans configuration relative to the carbonyl group. Furthermore, in formula (II), the dashed line indicates the attachment of $R^1$ to the nitrogen of the amide moiety of the repeating unit of formula (I). In formula (V), the dashed line indicates the attachment of $R^5$ to the nitrogen of the amide moiety of the repeating unit of formula (IV).

The radically polymerizable polyacidic polymer having repeating units of formula (I) is water-soluble and is reactive with a particulate glass in a cement reaction, whereby the radically polymerizable polyacidic polymer has a polymer backbone and hydrolysis-stable pendant groups $R^1$ having one or more radically polymerizable carbon-carbon double bonds.

It was surprisingly found that dental compositions, such as resin modified dental cement compositions, are subject to deterioration during storage or after curing in the mouth of the patient, wherein the deterioration includes hydrolytic degradation of the resin component conventionally containing hydrolyzable moieties. It has been recognized that by using the radically polymerizable polyacidic polymer having repeating units of formula (I), the drawbacks of conventional dental compositions, such as resin modified dental cement compositions known from the prior art, can be overcome.

The polymerizable pendant groups $R^1$ of the radically polymerizable polyacidic polymer having repeating units of formula (I) may react with a monomer having a radically polymerizable double bond, whereby a graft polymer is formed. The grafted side-chains may contain additional carboxylic acid groups which can take part in a cement reaction, thereby further increasing the strength of the cured composition.

In formula (II), Ar is an aromatic group which may be further substituted. The aromatic group is not specifically limited and may be any organic aromatic group, i.e. a cyclic moiety which number of π-electrons equals 4n+2, where n is zero or any positive integer. Preferably, Ar is derived from an arene or heteroarene. An arene is a monoyclic or polycycic aromatic hydrocarbon. A heteroarene is a heterocyclic compound formally derived from arenes by replacement of one or more methine (—C═) and/or vinylene (—CH═CH—) groups by trivalent or divalent heteroatoms, respectively, in such a way as to maintain the continuous π-electron system characteristic of aromatic systems and a number of out-of-plane r-electrons corresponding to the Hückel rule (4 n+2).

In case o+n is 2, Ar is preferably a $C_{6-14}$ arenetriyl or $C_{3-14}$ heteroarenetriyl group which may be further substituted by one or more substituents. In case o+n is 3, Ar is preferably a $C_{6-14}$ arenetetrayl or $C_{3-14}$ heteroarenetetrayl group which may be further substituted by one or more additional substituents. In case o+n is 4, Ar is preferably a $C_{6-14}$ arenepentayl or $C_{3-14}$ heteroarenepentayl group which may be further substituted by one or more additional substituents. In case o+n is 5, then Ar is preferably a $C_{6-14}$ arenehexayl or $C_{3-14}$ heteroarenehexayl group which may be further substituted by one or more additional substituent.

The additional substituents are selected from the group consisting of a straight chain or branched $C_1$ to $C_{10}$ alkyl group, a straight chain or branched $C_1$ to $C_{10}$ alkenyl group, —COOM, —$PO_3M$, —O—$PO_3M_2$ and —$SO_3M$, wherein M represents a hydrogen atom or a metal atom. More preferably, Ar is a $C_{6-10}$ arenetriyl or $C_{3-9}$ heteroarenetriyl group which may be substituted by one or more additional substituents selected from a straight chain or branched $C_1$ to $C_4$ alkyl group and a straight chain or branched $C_1$ to $C_4$ alkenyl group. Even more preferably, Ar is selected from a benzenetriyl group, a naphtalenetriyl group, a toluenetriyl group, a xylenetriyl group and a styrenetriyl group, and the heteroaryl group is a pyridinetriyl group. Yet even more preferably, Ar is a benzenetriyl group. Most preferably, Ar is a benzenetriyl group wherein a hydroxyl group is present in formula (i) in para-position to the methylene group linking $R^1$.

In formula (II), $R^2$ and $R^3$, which may be the same or different, independently represent a hydrogen atom, or a $C_{1-6}$ alkyl group which may be substituted with a carboxylic acid group. Preferably, $R^2$ and $R^3$, which may be the same or different, independently represent a hydrogen atom or a $C_{1-3}$ alkyl group. More preferably, $R^2$ represents a hydrogen atom or a methyl group, and $R^3$ represents a hydrogen atom. Most preferably, both $R^2$ and $R^3$ represent a hydrogen atom.

In formula (II), one or more R may be present depending on the value of n. The R may be the same or different when more than one R is present. R represents a hydrogen atom, a carboxylic acid group, a $COOR^a$ group, a $CONHR^b$ group, or a $CONR^c_2$ group. $R^a$, $R^b$, and $R^c$ represent a $C_{1-6}$ alkyl group. According to a preferred embodiment, R represents a hydrogen atom.

In formula (II), $R^8$ represents an electron donating group which activates the aryl group. Accordingly, each $R^8$ is directly bonded to a ring atom of the Ar group. $R^8$ may be a halogen atom or a group selected from —OH, —$OR_d$, —$NR^eH$, —$NR^eR^f$, —SH, and —$SR^9$, wherein $R^d$, $R^e$, $R^f$, $R^g$ and $R^g$ represent a $C_{1-6}$ alkyl group. Preferably, $R^8$ is a hydroxyl group. The halogen atom may be a fluorine atom, a chlorine atom, a bromine atom or an iodine atom. When o is 2, the $R_8$ cannot be both OH.

In formula (I), o is an integer of 1 or 2. Preferably, o is 1. In formula (II), n is an integer of 1 to 4. Preferably, n is an integer of 1 or 2. In formula (II), o+n is preferably 5 or less, more preferably 4 or less, in particular 3.

It is preferred that in formula (II), Ar is a phenyl group. Specifically, $R^1$ preferably represents a group of the following formula (II'):

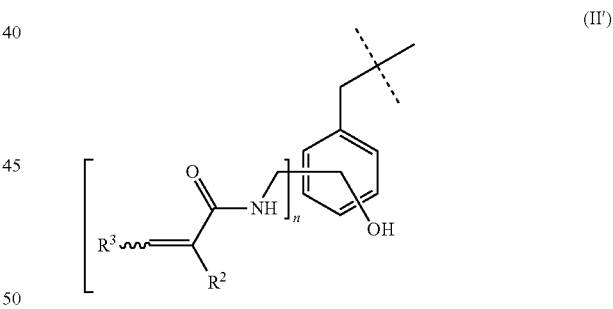

(II')

wherein $R^2$, $R^3$ and n are as defined as above.

It is particularly preferred that R is a group of the following formula ($II''_a$) or ($II''_b$):

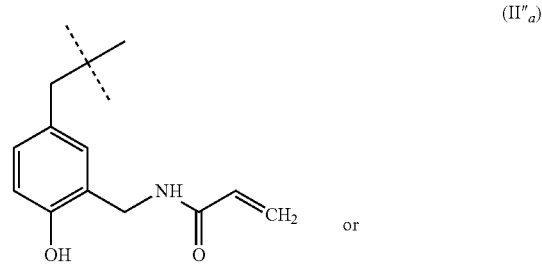

($II''_a$)

or

-continued

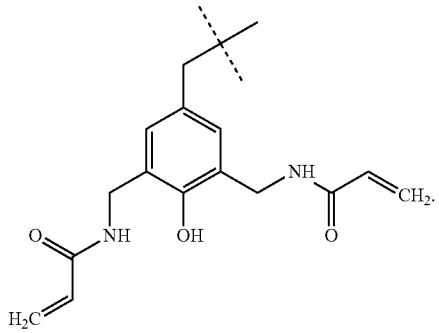
(II″b)

Furthermore, it is preferred that the radically polymerizable polyacidic polymer having repeating units of formula (I) further comprises acidic repeating units of the following formula (III):

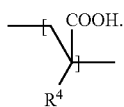
(III)

In formula (III), $R^4$ represents a hydrogen atom, or a $C_{1-6}$ alkyl group which may be substituted with a carboxylic acid group. Preferably, $R^4$ represents a hydrogen atom, or a $C_{1-3}$ alkyl group which may be substituted with a carboxylic acid group, more preferably $R^4$ represents a hydrogen atom or a methyl group. Most preferably, $R^4$ represents a hydrogen atom.

In the radically polymerizable polyacidic polymer having repeating units of formula (I), the molar ratio of repeating units of formula (III) and repeating units of formula (I) ([formula (III)]/[formula (I)]) is preferably in the range of 1000:1 to 1:1, more preferably 100:1 to 5:1, most preferably 50:1 to 10:1.

The radically polymerizable polyacidic polymer having repeating units of formula (I) preferably has a molecular weight $M_w$ in the range of 10,000 to 250,000, more preferably 20,000 to 150,000, most preferably 30,000 to 100,000.

The radically polymerizable polyacidic polymer having repeating units of formula (I) is hydrolysis stable, which means that it does not contain groups hydrolysing at pH 2.5 within one month when stored at a temperature of 50° C.

According to a particularly preferred embodiment, the radically polymerzable polyacidic polymer has repeating units of the following formula (I):

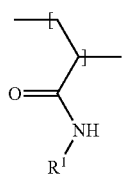
(I)

wherein $R^1$ represents a group of the following formula (II'):

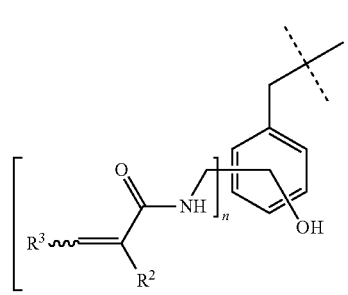
(II')

wherein
$R^2$ and $R^3$,
which may be the same or different, independently represent a hydrogen atom, or a $C_{1-4}$ alkyl group preferably $R^2$ is a hydrogen atom or a methyl group and $R^3$ is a hydrogen atom, and
n is an integer of 1 to 3, preferably n is an integer of 1 or 2,
which radically polymerizable polyacidic polymer further comprises acidic repeating units of the following formula (III):

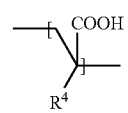
(III)

wherein
$R^4$ represents a hydrogen atom, or a $C_{1-4}$ alkyl group, preferably $R^4$ represents a hydrogen atom or a methyl group
wherein the molar ratio of repeating units of formula (III) and repeating units of formula (I)([formula (III)]/[formula (I)]) is in the range of 100:1 to 5:1, preferably 50:1 to 10:1, and the molecular weight $M_w$ is in the range of 20,000 to 150,000, preferably 30,000 to 100,000.

The process for preparing a radically polymerizable polyacidic polymer having repeating units of formula (I) comprises reacting a polyacidic polymer having repeating units of the following formula (IV):

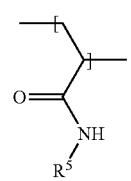
(IV)

wherein $R^5$ represents a group of the following formula (V):

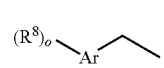
(V)

wherein

Ar is an aromatic group which may be further substituted;

$R^5$ represents a halogen atom or a group selected from —OH, —$OR^d$, —$NR^eH$, —$NR^eR^f$, —SH, and —$SR^g$, wherein $R^d$, $R^e$, $R^f$, $R^g$, and $R^g$ represent a $C_{1-6}$ alkyl group; and o is an integer of 1 or 2, provided that when o is 2, the $R^8$ cannot be both OH, with a compound of the following formula (VI)

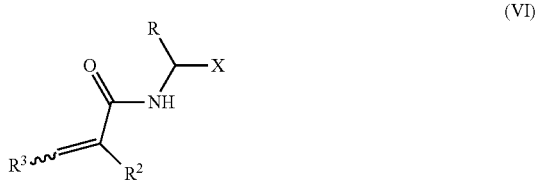

wherein X is a leaving group, and

R, $R^2$ and $R^3$, which may be the same or different, independently represent a hydrogen atom, or a $C_{1-6}$ alkyl group which may be substituted with a carboxylic acid group.

In compound of formula (VI), leaving group X is preferably a leaving group susceptible to C—C bond-formation by means of electrophlic aromatic substitution. More preferably, leaving group X is selected from the group consisting of a fluorine atom, a chlorine atom, a bromine atom or a hydroxyl group. Most preferably, leaving group X is a hydroxyl group.

The reaction conditions for polymer analogous reaction of the polyacidic polymer having repeating units of the formula (IV) with a compound of formula (VI) are not particularly limited.

Preferably, the reaction is carried out in the presence of a solvent. More preferably, the solvent is water.

The reaction temperature for reacting the polyacidic polymer having repeating units of formula (IV) with a compound of formula (VI) is not particularly limited. Preferably, the reaction is carried out at a temperature of between 20 to 90° C. Most preferably, the reaction temperature is in the range of from 40 to 80° C.

The reaction time for reacting the polyacidic polymer having repeating units of formula (IV) with a compound of formula (VI) is not particularly limited. Preferably, the reaction time is in the range of from 1 to 72 hours, most preferably 12 to 50 hours.

The molar ratio of polyacidic polymer having repeating units of formula (IV) to compound of formula (VI) is not particularly limited. Preferably, the molar ratio of polyacidic polymer having repeating units of formula (IV) to compound of formula (VI) is 1:5 to 1:1000, more preferably 1:100 to 1:800, most preferably 1:300 to 1:700.

Reacting of the polyacidic polymer having repeating units of formula (IV) with a compound of formula (VI) may be carried out in the presence of a catalyst, preferably a catalyst in the form of an organic or inorganic acid. More preferably, the catalyst is selected from the group consisting of hydrochloric acid, hydrobromic acid, hydrofluoric acid, phosphoric acid, sulphuric acid sulfamic acid, oxalic acid and p-toluenesulfonic acid. Most preferably, the catalyst is hydrochloric acid or oxalic acid. The amount of catalyst may be selected from 0.01 to 100 mol %, preferably from 10 to 90 mol %, more preferably from 30 to 80 mol % based on the molar amount of the polyacidic polymer having repeating units of formula (IV) and compound of formula (VI).

The number n of groups of formula (II) in $R^1$ of the reaction product in the form of the radically polymerizable polyacidic polymer having repeating units of formula (I) may be set by suitably selecting the reaction conditions for reacting the polyacidic polymer having repeating units of formula (IV) with the compound of formula (VI). For example, for setting n=1, oxalic acid may be applied as the catalyst, and the reaction temperature is preferably within a range of 60 to 80° C. For setting n=2, hydrochloric acid may be applied as the catalyst, and the reaction temperature is preferably within a range of 35 to 55° C.

The reaction product obtained from reacting the polyacidic polymer having repeating units of formula (IV) with a compound of formula (VI) may be purified according to conventional methods. Preferably, the reaction product in the form of the radically polymerizable polyacidic polymer having repeating units of formula (I) is separated from the reaction mixture and purified by dialysis against water, more preferably the dialysis is carried out with a size exclusion of molecules having a molecular weight of up to 2000 g/mol. Owing to the purification by means of dialysis, or well-known polymer-chemically purification methods such as precipitation, liquid-liquid extraction. The radically polymerizable polyacidic polymer having repeating units of formula (I) is obtained in both high yields and purity.

According to a particularly preferred embodiment, the process for preparing a radically polymerizable polyacidic polymer having repeating units of formula (I) comprises reacting a polyacidic polymer having repeating units of the following formula (IV):

wherein $R^5$ represents a group of the following formula (V):

with a compound of the following formula (VIa)

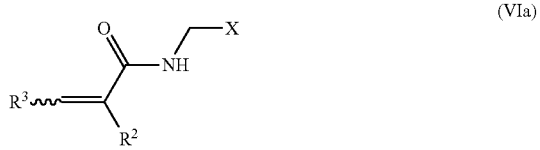

wherein X is a hydroxyl group, $R^2$ is a hydrogen atom or a methyl group, preferably a hydrogen atom, and $R^1$ is a hydrogen atom, in water as the solvent and in the presence of a catalyst selected from the group consisting of hydrochloric acid, hydrobromic acid, hydrofluoric acid, phosphoric acid, sulphuric acid, sulfamic acid, oxalic acid and p-toluenesulfonic acid, preferably the catalyst is hydrochloric acid or oxalic acid,
wherein the amount of catalyst may be selected from 10 to 90 mol %, preferably from 30 to 80 mol % based on the molar amount of the polyacidic polymer having repeating units of formula (IV) and compound of formula (VIa),
wherein the reaction temperature is in the range of from 40 to 80° C., and
the molar ratio of polyacidic polymer having repeating units of formula (IV) to compound of formula (VIa) is 1:100 to 1:800, preferably 1:300 to 1:700.

A starting material in the form of the polyacidic polymer having repeating units of formula (IV) may be provided by polymerizing a monomer represented by the following formula (VII):

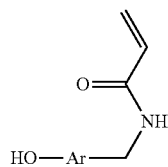

(VII)

wherein
Ar is an aromatic group as defined above for formula (II). Alternatively, the substitution pattern of the aromatic group may be adapted to the desired copolymer.

Preferably, the starting material in the form of the polyacidic polymer having repeating units of formula (IV) is an acrylic acid derivative copolymer having repeating units of formulae (IV) and (III) which may be obtained by copolymerizing a monomer represented by the following formula (VII):

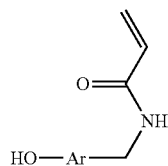

(VII)

wherein
Ar is an aromatic group as defined above, with a monomer represented by the following formula (VIII)

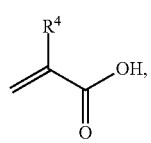

(VIII)

wherein $R^4$ is defined as above for formula (III).

The carboxylic acid group(s) optionally comprised in the monomer represented by formula (VI) and/or comprised in the monomer represented by formula (VIII) may optionally be protected.

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylakyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxy-protecting group is a tert-butyl group.

The optionally protected carboxylic acid group(s) can be deprotected prior to polymerization or copolymerization of the monomer represented by formula (VII), concomitant thereto or subsequently thereto.

The conditions for deprotection of the optionally protected carboxylic acid group(s) are selected according to the protecting group used. Preferably, the protected carboxylic acid group(s) is/are deprotected by hydrogenolysis or treatment with acid or base.

If the deprotection of the optionally protected carboxylic acid group(s) is carried out concomitantly with polymerization or copolymerization of the monomer represented by formula (VII), it will be understood by a person skilled in the art that the deprotection conditions and the conditions for the polymerization or copolymerization have to be selected so that both reactions can proceed efficiently.

The reaction conditions for polymerizing or copolymerizing the monomer represented by formula (VII) are not particularly limited. Accordingly, it is possible to carry out the reaction in the presence or absence of a solvent. Preferably, the reaction is carried out in the presence of a solvent. A suitable solvent may be selected from the group of water, dimethyl formamide (DMF), tetrahydrofurane (THF), and dioxane. Preferably, the solvent is dioxane.

The reaction temperature for polymerizing or copolymerizing the monomer represented by formula (VII) is not particularly limited. Preferably, the reaction is carried out at a temperature of between −10° C. to the boiling point of the solvent. More preferably, the reaction temperature is in the range of from 0 to 110° C., even more preferably 40 to 100° C., most preferably 60 to 90° C.

The reaction time for polymerizing or copolymerizing the monomer represented by formula (VII) is not particularly limited. Preferably, the reaction time is in the range of from 10 minutes to 48 hours, more preferably 1 hour to 36 hours, even more preferably 2 to 24 hours, most preferably 3 to 12 hours.

The reaction for polymerizing or copolymerizing the monomer represented by formula (VII) is preferably carried out in the presence of a polymerization initiator. Preferably, the polymerization initiator is selected from azobisisobutyronitrile (AIBN), 2,2-azobis(2-amidinopropane)dihydrochloride, 2,2'-azobis(2-methylbutyronitrile), 2,2'-azobis(N, N'-dimethyleneisobutyramidine) dihydrochoride, and 4,4'-azobis(4-cyano pentanoic acid), most preferably, the polymerization initiator is AIBN. The amount of the polymerization initiator is not particularly limited. Suitably, the amount is in the range of from 0.001 to 5 mol % based on the total amount of the monomers.

The reaction for copolymerizing the monomer represented by formula (VII) and the monomer represented by formula (VIII) is preferably carried out by providing the monomer represented by the formula VII and the monomer represented by the formula VIII in the molar ratio ([formula (VII)]/[formula (VIII)]) in the range of 1000:1 to 1:1, more preferably 100:1 to 5:1, most preferably 50:1 to 10:1.

In the acrylic acid derivative copolymer having repeating units of formulae (IV) and (III), the molar ratio of repeating units of formula (II) and repeating units of formula (IV) ([formula (III)]/[formula (IV)]) is preferably in the range of 1000:1 to 1:1, more preferably 100:1 to 5:1, most preferably 50:1 to 10:1.

The reaction product obtained from polymerizing or copolymerizing the monomer represented by formula (VII) may be isolated by precipitation and filtration, or lyophilisation, preferably by precipitation and filtration. The reaction product may be purified according to conventional methods. It was surprisingly found that the reaction product can be obtained in both high yield and purity simply by dissolving and precipitating the reaction product, preferably twice. Hence, it can be dispensed with elaborate purification of the reaction product. For example, the crude reaction product may be dissolved in a suitable organic solvent, e.g. in dioxane, and precipitated by adding a suitable organic solvent, e.g. acetonitrile.

The acrylic acid derivative copolymer having repeating units of formulae (IV) and (III) may be a statistical copolymer, a random copolymer, an alternating copolymer, a block copolymer or a combination thereof. Preferably, it is a statistical copolymer.

Preferably, in the acrylic acid derivative copolymer having repeating units of formulae (IV) and (III), $R^1$ represents a group of the following formula (V'):

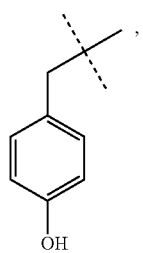

(V')

and
$R^4$ represents a hydrogen atom.

The monomer represented by the formula (VII) may be prepared by reacting a compound of the following formula (IX)

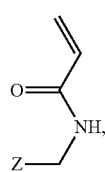

(IX)

wherein Z is a leaving group,
with a compound of formula (X)

Ar—OH     (X), wherein Ar is an aromatic group as defined above for formula (II).

Preferably, leaving group Z of compound of formula (IX) is a leaving group susceptible to C—C bond-formation by means of electrophilic aromatic substitution. More preferably, leaving group Z is selected from the group consisting of a fluorine atom, a chlorine atom, a bromine atom or a hydroxyl group. Most preferably, leaving group Z is a hydroxyl group.

The reaction conditions for reacting the compound of formula (IX) with the compound of formula (X) are not particularly limited.

The reaction may be carried out in the absence or presence of a solvent, preferably in the presence of a solvent. The solvent is preferably selected from the group consisting of acetone, THF, ethyl acetate, chloroform, 1,2-dichlorethane. Most preferably, the solvent is acetone.

The reaction temperature for reacting the compound of formula (IX) with the compound of formula (X) is not particularly limited. Preferably, the reaction is carried out at a temperature of between −10 to 70° C. More preferably, the reaction temperature is in the range of from 10 to 60° C., most preferably from 30 to 50° C.

The reacting of the compound of formula (IX) with the compound of formula (X) may be carried out in the presence of a catalyst, preferably in the form of an organic or inorganic acid. More preferably, the catalyst is an inorganic Lewis acid, that is an inorganic electron acceptor. Even more preferably, the catalyst is selected from the group consisting of $AlCl_3$, $BF_3$, $FeCl_3$, $FeCl_3$, $FeBr^3$, $FeBr_2$, $FeSO_4$, $Fe_2(SO_4)_3$, $ZnCl_2$, $ZnBr_2$, $ZnSO_4$. Yet even more preferably, the catalyst is selected from the group consisting of $AlCl_3$, $BF_3$ and $FeCl_3$. Most preferably, the catalyst is $AlCl_3$. The amount of catalyst may be selected from 0.01 to 150 mol %, preferably from 30 to 130 mol %, more preferably from 60 to 120 mol %, most preferably from 90 to 110 mol % based on the molar amount of compound of formula (IX).

Furthermore, when reacting the compound of formula (IX) with the compound of formula (X), an antioxidant may be added which suppresses polymerisation and/or autoxidation of compound of formula (IX). Preferably, the antioxidant is selected from the group consisting of 3,5-die-tert-4-butylhydroxytoluene (BHT), 4-tert-butylcatechol, phenothioazine, tert.-buty hydroquinone (TBHQ) and hydroxytoluene. Most preferably, the antioxidant is phenothioazine. The amount of antioxidant may be selected from 0.001 to 2% and preferably from 0.02 to 0.5% based on the total weight of compound of formula (IX).

The reacting of the compound of formula (IX) with the compound of formula (X) is not particularly limited. Preferably, the reaction time is in the range of from 10 minutes to 48 hours, more preferably 1 hour to 36 hours, most preferably 2 to 24 hours.

The product obtained by reacting the compound of formula (IX) with the compound of formula (X) may be isolated from the crude reaction mixture by extraction with an organic solvent, preferably chloroform or dichloromethane. The product may be purified according to conventional methods, preferably by silica-gel column chromatography.

The Redox Initiator System (ii)

The dental composition according to the present invention comprises a redox initiator system (ii).

The redox initiator system (ii) comprises
  (a) one or more clathrate compounds comprising
    (a1) a host molecule and
    (a2) one or more guest molecules being reducing agent(s), and
  (b) an oxidizing agent.

In the redox initiator system (ii), the host molecule is selected from cyclodextrines, crown ethers, cucurbituries and calixarenes, and the one or more guest molecules are reducing agents.

For the host molecule (a1), the cyclodextrines are preferably natural, non-reduced oligo-saccharides in which glucose is linked in a cyclic form through α-1,4-linkage. Such natural cyclodextrin preferably contains 5 to 8 glucose moieties.

The one or more guest molecule(s) (a2) selected from reducing agents. The reducing agent (a2) is not specifically limited and may be any organic or inorganic reducing agent being capable of reacting in a redox reaction with a peroxide or hydroperoxide. Preferably, the reducing agent is a liquid at room temperature (e.g. 25° C.).

Advantageously, by forming a clathrate compound (a), a liquid reducing agent can be transformed into a solid. This renders possible to add a liquid reducing agent to a part or pack of the dental composition comprising only solid components.

Clathrate synthesis leads to the formation of structures having defined stoichiometry between host and guest molecules.

Preferably, the reducing agent is an aromatic tertiary amine, an aromatic tertiary phosphine or a borane. Preferably, the reducing agent is a liquid at room temperature (e.g. 25° C.). Preferably, the clathrate compound is a solid at room temperature (e.g. 25° C.), whereby the clathrate is incorporated into a powder component of a two-part dental composition.

More preferably, the reducing agent is an aromatic tertiary amine and most preferably the reducing agent is an aromatic tertiary amine of the following formula (XI):

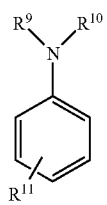

(XI)

wherein
$R^9$ and $R^{10}$ which may be the same or different, independently represent straight chain, branched or cyclic $C_{1-8}$ alkyl group, or $R^9$ and $R^{10}$ form together with the nitrogen atom to which they are bonded a 3-8 membered saturated heterocyclic ring; and
$R^{11}$ represents an organic group such as, for example, a $C_{1-10}$ hydrocarbyl group which may contain 1 to 4 heteroatoms selected from oxygen and sulfur atoms. Preferably, $R^{11}$ is a straight chain, branched or cyclic $C_{1-8}$ alkyl, $C_{1-8}$ thioalkyl or $C_{1-8}$ alkyloxy group, a $C_{1-8}$ aryl group, $COOOC_{1-8}$, CN, $OC_{1-8}$, halogen, amide or araliphatic group.

Particularly preferred aromatic tertiary amines are selected from the group consisting of 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene, 4-tert.-butyl-N,N-dimethylaniline. In particular, the aromatic tertiary amine is selected from the group consisting of methyl 4-N,N-dimethylaminobenzoate, ethyl 4-N,N-dimethylaminobenzoate, 4-N,N-dimethylaminoethyl methacrylate, isoamyl 4-N,N-dimethylaminobenzoate and 4-tert.-butyl-N,N-dimethylaniline. Most preferably, the aromatic tertiary amine is 4-tert.-butyl-N,N-dimethylaniline.

Preferably, the aromatic tertiary amine is a liquid at room temperature (e.g. 25° C.). Preferably, the clathrate compound is a solid at room temperature (e.g. 25° C.), whereby the clathrate is incorporated into a powder component of a two-part dental composition. Accordingly, it is possible to include a liquid reducing agent into a powder composition without losing any of the activity of the reducing agent in a redox initiator system of a dental composition.

Preferred aromatic tertiary phosphine compounds have the following formula (X):

(XII)

wherein
$Z^P$ is a group of the following formula (XIII)

(XIII)

wherein
R* represents a substituted or unsubstituted hydrocarbyl group;
$Ar^P$ represents a substituted or unsubstituted aryl or heteroaryl group;
$R^P$ is an aryl group, which may be substituted by one or more groups selected from a hydroxyl group, an amino group, a —$NR^aR^b$ group (wherein $R^a$ and $R^b$, which may be the same or different, are selected from $C_{1-6}$ alkyl groups), a carboxyl group, and a group having a polymerizable double bond;
wherein the group R* and $Ar^P$ may be substituted by one or more groups selected from a hydroxyl group, an oxo group, a —$NR_aR_b$ group (wherein $R_a$ and $R_b$, which may be the same or different, are selected from a hydrogen atom and $C_{1-6}$ alkyl groups), a carboxyl group, and a group having a polymerizable double bond, and
$L^P$ may be substituted by one or more groups selected from a hydroxyl group, an oxo group, a —$NR_aR_b$, group (wherein $R_a$ and $R_b$, which may be the same or different, are selected from a hydrogen atom and $C_{1-6}$ alkyl groups), a carboxyl group, and a group having a polymerizable double bond.

In formula (XII), for R*, the monovalent hydrocarbyl group may be an alkyl group, a cycloalkyl group, a cycloalkylalkyl group, an arylalkyl group or an aryl group.

$Ar^P$ represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

$L^P$ is a substituted or unsubstituted divalent hydrocarbyl group which may contain a linkage selected from an ether linkage, a thioether linkage, an ester linkage, an amide linkage, and a urethane linkage. For $L^P$, the divalent hydrocarbyl group may be an alkyldiyl group, a cycloalkyldiyl group, a cycloalkylalkyl-diyl group, an arylalkyl-diyl group or an aryldlyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alky(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalky(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloakylalkyl(-diyl) group can for example, include methylcyclopropyl(-diyl)methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propycyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-6}$ alkyl(diyl) group and the $C_{3-14}$ cycloalkyl(diyl) group may optionally be substituted by one or more members of the group selected from a $C_{1-4}$ alkyl group, $C_{1-4}$alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (XII), any of the hydrocarbyl group may be substituted by one or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifuoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

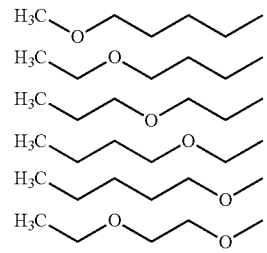

In formula (XII), group R* and/or $Ar^P$ as well as $R^P$ and/or may be substituted with a polymnerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, R* and $Ar^P$ independently are aromatic hydrocarbyl groups selected from a phenyl group, a naphtyl group, a tolyl group, a xylyl group, and a styryl group.

As regards $R^P$, this moiety is an aryl group, which may be substituted by one or more groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizabie double bond. According to a preferred embodiment, $R^P$ is an aryl group substituted by one or more groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizable double bond. More preferably. $R^P$ is a phenyl group substituted by one or two groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizable double bond.

Even more preferably, the aromatic phosphine compound is a compound of formula (XII) wherein $Z^P$ is a group of the following formula:

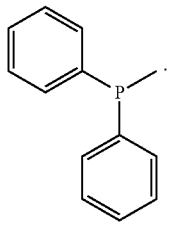

Specific examples for a compound of formula (XIX) include triphenyl phosphine (TPP), 4-(diphenylphosphino) styrene (DPPS), 4-(diphenylphosphino)benzoic acid, 4-(diphenyl-phosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(di-phenylphosphino)phenyl]ether (BDPPE), (4-Hydroxyphenyl)diphenyphosphine, allyldiphenylphosphine. Preferably, the compound of formula (XIX) is triphenyl phosphine (TPP) or 4-(diphenylphos-phino)styrene (DPPS), more preferably 4-(diphenylphos-phino)styrene (DPPS).

From the above listed aromatic tertiary compounds of formula (XII), 4-(diphenylphos-phino)styrene (DPPS) is particularly preferred, since this compound provides for particularly improved photo-bleaching results compared to the already advantageous results obtained with triphenyl phosphine (TPP).

A compound of the formula (XII) may be a known compound which is commercially available or may be prepared according to published procedures, as described for example in WOs2016/156363 A1.

Preferred borane compounds have the following formula (XIV):

wherein
$R^{12}$, $R^{13}$ and $R^{14}$ may be the same or different, independently represent a $C_{1-6}$ alkyl group, or a $C_{4-10}$ aryl or heteroaryl group.

The oxidizing agent is preferably a peroxide or hydroperoxide.

Preferably, the peroxide or hydroperoxide is selected from cumyl hydroperoxide, tert-butyl peroxybenzoate, tert-butylperoxy (2-ethythexyl)carbonate, tert-butylhydroperoxide, di(tert-butyl)peroxide, tert-butylperoxy-3,5,5-trimethylhexanoate and potassium peroxydisulfate. More preferably, the peroxide or hydroperoxide is selected from cumyl hydroperoxide, tert-butyl peroxybenzoate and potassium peroxydisulfate. Most preferably, the peroxide or hydroperoxide is potassium peroxydisulfate.

Optionally, the redox initiator system (ii) comprises one or more inorganic catalysts and/or organic polymerization accelerators.

Preferably, the catalyst is a metal salt, more preferably a transition metal salt. Even more preferably, the catalyst is a transition metal salt of V, Fe, Cu, Ti, Mn, Ni and Zn. Most preferably, the catalyst is a transition metal salt of Fe or Cu. Tetravalent and/or pentavalent vanadium compounds are preferred, including vanadium(IV) oxide, vanady(IV) acetylacetonate, vanadyl(IV) oxalate, vanadyl(IV) sulfate, oxobis(1-pheny-1,3-butanedionato)vanadium(IV), bis(maltolato) oxovanadium(IV), vanadium(V) oxide, sodium metavanadate(V), and ammonium metavanadate(V). Examples of the copper compounds include copper acetylacetonate, copper(II) acetate, copper oleate, copper(II) chloride, and copper(II) bromide.

Preferably, the polymerization accelerator is selected from sufinic acids, sulfinates, sulfites, hydrogen sulfites, aldehydes, thiourea compounds, barbituric acid derivatives, triazine compounds, halogen compounds, and thiol compounds Examples of the suffinic acids and sulfinates that may be used as the polymerization accelerator include p-toluenesulfinic acid, sodium p-toluenesulfinate, potassium p-toluenesulfinate, calcium p-toluenesulfinate, benzenesulfinic acid, sodium benzenesulfinate, potassium benzenesulfinate, calcium benzenesufinate, 2,4,6-trimethylbenzenesufinic acid, sodium 2,4,6-trimethylbenzenesulfinate, potassium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, and calcium 2,4,6-triisopropylbenzenesulfinate. Among these, sodium p-toluenesulfinate, sodium benzenesulfinate, and sodium 2,4,6-triisopropylbenzenesuffinate are preferred.

Examples of the sulfites and hydrogen sulfites that may be used as the polymerization accelerator include sodium sulfite, potassium sulfite, calcium sulfite, ammonium sulfite, sodium hydrogen sulfite, and potassium hydrogen sulfite.

Examples of the aldehydes that may be used as the polymerization accelerator include terephthalaldehydes; and benzaldehyde derivatives such as dimethylaminobenzaidehyde, p-methyloxybenzaldehyde, p-ethyloxybenzaldehyde, and p-n-octyloxybenzadehyde.

Examples of the thiourea compounds that may be used as the polymerization accelerator include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, triethylthiourea, tri-n-propylthiourea, tricyclohexylthiourea, tetramethylthiourea, tetraethylthiourea, tetra-n-propylthiourea, tetracyclohexylthiourea, 3,3-dimethylethylenethiourea, and 4,4-dimethyl-2-imidazolinethione.

The content of the polymerization accelerator is preferably 0.01 to 5 wt %, and more preferably 0.05 to 3 wt % with respect to the total dental polymerizable composition of the present invention.

For the one or more clathrate compounds (a), it is preferred that the molar ratio of the guest molecules (a2):the host molecules (a1) is in the range of from 1:05 to 1:3.

The dental composition according to the present invention may be a two-pack or a multi-pack dental composition.

The term "two-pack" or "multi-pack" as used herein means that the components of the dental composition are comprised in two or more separate packs. For example, a first part of components is comprised in a first pack, while as second part of components is comprised in a second pack, a third part of components may be comprised in a third pack, a fourth part of components may be comprised in a fourth pack, and so on.

Preferably, the dental composition is a two-pack dental composition.

For the two-pack dental composition, it is preferred that the first part comprises at least the redox initiator system (ii), and optionally further solid components such as dental fillers, e.g. particulate glass filler. The second part preferably comprises at least the radically polymerizable compound (i), and optionally water and organic solvent(s).

Irrespective whether the dental composition is in the form a two-pack or multi-pack, it is preferred that the redox initiator system (ii) including the one or more clathrate compounds (a) and the reducing agent (b) are stored as a mixture in a single pack.

It is preferred that the dental composition according to the present invention has a working time of at least 2 and less than 4 minutes at 23° C.

Furthermore, it is preferred that the dental composition according to the present invention has a setting time of 2 to 6 minutes at 37° C.

The present inventors surprisingly found that by providing a dental composition having a redox initiator system in which the reducing agent is stabilised in the form of a clathrate compound (a), not only excellent storage stability, but also outstanding working time and setting time are provided. This renders possible a significantly easier application of the dental composition according to the present invention compared with conventional dental compositions based on organic peroxides and organic hydroperoxides.

The redox initiator system (ii) may be the only initiator system of the dental composition.

Alternatively, the dental composition may comprise a dual cure initiator system containing the redox initiator system (ii) and a photoinitiator system. The photoinitiator system may comprise one or more photoinitiators.

The term "photoinitiator" as used herein means any chemical compound that forms free radicals when activated, e.g. by exposure to light or interaction with a coinitiator in a photochemical process.

"Actinic radiation" is any electromagnetic radiation that is capable of producing photochemical action and can have a wavelength of at least 150 nm and up to and including 1250 nm, and typically at least 300 nm and up to and including 750 nm.

The term "photocuring" means the polymerization of functional polymerizable compounds such as monomers, oligomers or even polymers, into a crosslinked polymer network by means of a photoinitiator.

For example, a suitable photoinitiator system may be in the form of a binary or tertiary system. A binary systems may include a photoinitiator and an electron donor compound, and a tertiary system may include a photoinitiator, an electron donor compound and a coinitiator in the form of an iodonium, sulfonium or phosphonium salt, as for example described in U.S. Pat. No. 5,545,676.

For example, suitable photoinitiators are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

Another suitable photoinitiator for the photoinitiator system is represented by phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoydiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyidiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide. Examples of suitable tertiary amine reducing agents include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethy)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino)benzoate and N,N-dimethylaminoethyl methacrylate. Examples of an aliphatic tertiary amine include trimethylamine, triethylamine, N-methyidiethanolamine, N-ethyldiethanolamine, N-n-butyldiethanolamine, N-lauryidiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The photoinitiator system may further comprise a coinitiator.

The term "coinitiator" refers to a molecule that produces a chemical change in another molecule such as a photoinitiator in a photochemical process.

Preferably, the coinitiator is selected from diaryl iodonium salts, triaryl sulfonium salts and tetraaryl or tetraalkyl phosphonium salts.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafuoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethypyrazoyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred diaryl iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methypropyl)pheny]iodonium hexafluorophosphate (Irgacure® 250, commercial product available from BASF SE), (4-methylphenyl)[4-(2-methylpropyl) phenyl] iodonium tetrafluoroborate, 4-octyloxypheny phenyliodonium hexafluoroantimonate, 4-(2-hydroxytetradecyloxypheny)phenylodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methydiphenyliodonium tetrakis(pentafluorophenyl) borate.

A preferred triaryl sulfonium salt is S-(phenyl)thianthrenium hexafluorophosphate of the following formula:

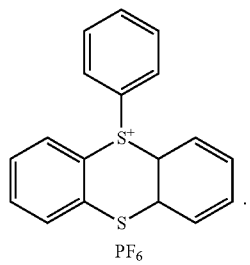

Particularly preferred phosphonium salts are the tetraalkyl phosphonium salts tetrakis-(hydroxymethy)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

Further Optional Components

The dental composition according to the present invention may, besides of the above described components, comprise additional optional components.

For example, the dental composition according to the present invention may comprise water.

The dental composition of the present invention may preferably comprise 5 to 20 percent by weight based on the total weight of the composition of water.

The dental composition according to the present invention may comprise (iii) one or more dental filler(s). Preferably, the dental filler(s) (iii) are selected from particulate glass fillers, silanated glass flakes, granulated prepolymerized filiers, ground prepoymerized fillers and filler aggregates.

The term "particulate glass filler" refers to a solid mixture of mainly metal oxides transformed by a thermal melt process into a glass and crushed by various processes. The glass is in particulate form. Moreover, the particulate glass filler may be surface modified, e.g. by silanation or acid treatment.

For the dental fillers, a glass component may be selected from "inert glass(es)", "reactive glass(es)" and "fluoride releasing glass(es)".

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318,929, 5,360,770, and application US 2004/0079258 A1. Specifically, from US 2004/0079258 A1, inert glasses are known in which strongly basic oxides such as CaO, BaO, SrO, MgO, ZnO, $Na_2O$, O, $K_2O$, $Li_2O$ etc. are replaced with weakly basic oxides such as those in the Scandium or Lanthanide series.

The term "reactive glass(es)" refers to a glass which is capable of reacting with a polymer containing acidic groups in a cement reaction. The glass is in particulate form. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

Preferably, the particulate glass filler is a reactive glass or a fluoride releasing glass as defined above, more preferably a reactive glass.

Most preferably, the particulate glass filler is a reactive particulate glass filler comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present dental composition preferably comprises 20 to 90 percent by weight of the particulate glass filler, more preferably 30 to 80 percent by weight, based on the total weight of the composition.

The particulate glass filler usually has an average particle size of from 0.005 to 100 µm, preferably of from 0.01 to 40 µm, more preferably of from 0.05 to 20 µm, most preferably of from 0.1 to 3 µm as measured, for example, by electron microscopy or by using a conventional laser diffraction particle sizing method as embodied by a MALVERN Mastersizer S or MALVERN Mastersizer 3000 apparatus.

The particulate glass filler may have a unimodal or multimodal (e.g, bimodal) particle size distribution, wherein a multimodal particulate glass filler represents a mixture of two or more particulate fractions having different average particle sizes.

The term "silanated" as used herein means that the dental filler has silane coupling agent(s) on its surface, for example in the form of a coating at least partly, and preferably fully covering the surface of the dental filler.

Typically, the silane coupling agent(s) are organosilanes of formula (Y)

$$(R_{10}, R_{11}, R_{12})Si(R_H)_n \qquad (Y)$$

are applied, wherein n is 1 to 3 and the number of substituents $R_{10}$, $R_{11}$, $R_{12}$ is 4−n, wherein at least one of $R_{10}$, $R_{11}$, $R_{12}$ represents a polymerizable group. $R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-18}$ or branched or cyclic $C_{3-8}$ alkyl groups. Most preferably, the hydrolysable group $R_H$ represents an alkoxy group.

The groups $R_{10}$, $R_{11}$, and $R_{12}$ may be the same or different and represent unreactive groups and/or polymerizable groups, with the proviso that at least one of $R^{10}$, $R_{11}$ and $R_{12}$ represents a polymerizable group. Unreactive groups for $R^{10}$, $R_{11}$ and $R_{12}$ may be represented by alkyl groups, preferably linear $C_{1-8}$ or branched or cyclic $C_{3-8}$ alkyl groups. Polymerizable groups for $R_{10}$, $R_{11}$ and $R_{12}$ are preferably selected from the group consisting of a (meth)acryl group, a vinyl group or an oxirane group, more preferably (meth)acryl group or a vinyl group, and most preferably a (meth)acryl group which may be in the form of e.g. methacryloxy or methacryoxyalkyl wherein alkyl means a linear $C_{1-8}$ or branched or cyclic $C_3$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0969789 A1, namely 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyl-dichloromonomethyl-silane and 3-methacryloxypropylmonochlorodimethylsilane.

Alternatively or additionally to the organosilanes of formula (Y), so-called dipodal organosilanes may be applied. Dipodal organosilanes are typically compounds of formula (Z)

$$((R_{10}, R_{11}, R_{12})Si—R_{13})_2CH—R_H \qquad (Z),$$

wherein $R_{10}$, $R_{11}$, $R_{12}$ and $R_H$ have the same meaning as defined above for the organosilane of formula (Y), and $R_{13}$ represents an alkylene group, preferably a linear $C_{1-8}$ or branched or cyclic $C_{3-8}$ alkylene group.

The term "flake" as used herein means that the glass is in the form of a flake, that is its long diameter is larger than its thickness, at least by factor 2. The ratio of average long diameter to average thickness is termed "average aspect ratio" herein.

The aforementioned filler aggregates may be obtained by a process comprising:
(a) coating a particulate filler, preferably a particulate glass filler as described above, which has a median particle size (D50) of from 1 to 1200 nm, with a coating composition containing a polymerizable film-forming agent forming a polymer coating layer on the surface of the particulate filler, said polymer coating layer may display reactive groups on the surface of the coating layer, said reactive groups being selected from addition polymerizable groups and step-growth polymerizable groups, thereby forming a coated particulate filler; subsequently or concurrently
(b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosinking agent;
(c) optionally milling, classifying and/or sieving the granulation of the coated particulate filler; and
(d) optionally further crosslinking the granulation of the coated particulate filler; for providing composite filler particles having a median particle size (D50) of from 1 to 70 µm, wherein reactive groups are transformed into crossinking groups obtained by reacting reactive groups and optionally a further crosslinking agent, and wherein the particulate filler is the main component by volume of the composite filler particles as further described in EP 2 604 247 A1.

For obtaining granulated and ground prepolymerized fillers, step (b) of the above described process is omitted, and the milling step (c) is applied with a suitable milling apparatus to attain an appropriate granulation particle size or ground particle size.

The dental composition according to the present invention preferably contains the dental filler in an amount of 1 to 85 percent by weight based on the total weight of the composition.

According to particular preferred embodiment, the dental composition according to the present invention comprises a dental filler (iii) containing
(iii-1) one or more particulate glass filler(s) having an average particle size of from 0.1 to 3 µm; and
(iii-2) one or more silanated glass flake(s),
(a) wherein the silanated glass flakes have an average thickness between 50 nm and 1000 nm; and (b) wherein the silanated glass flakes have an average aspect ratio (long diameter/thickness) in the range of from 2:1 to 50:1.

The "average thickness" as used herein may be determined as follows: The thicknesses of 100 or more glass flakes of a sample are determined by scanning electron microscopy (SEM). Then, the total of the measured thicknesses is devided by the number of glass flakes for which the thickness was determined.

In the dental filler (iii), the particulate glass filler (iii-1) has an average particle size of from 0.1 to 3 μm, preferably 0.2 to 2 μm, more preferably from 0.3 to 1.5 μm, most preferably from 0.5 to 1.2 μm. When the average particle size of the particulate glass filler (iii-1) is less than 0.1 μm, then the handling properties of the dental composition may deteriorate. When the average particle size of the particulate glass filler (iii-1) is more than 3.0 μm, then the gloss properties of the cured dental composition may deteriorate.

Preferably, the particulate glass filler (iii-1) is a reactive glass or a fluoride releasing glass. More preferably, the particulate glass filler (iii-1) is a reactive glass.

Preferably, the dental composition contains the particulate glass filler (iii-1) in an amount of 0.5 to 60 percent by weight, preferably 1 to 50 percent by weight, more preferably 3 to 40 percent by weight based on the total weight of the composition.

The particulate glass filler (iii-1) preferably has a sphericity of at least 0.5, more preferably at least 0.9, and most preferably at least 0.95.

The term "sphericity" as used herein means the ratio of the surface area of a sphere with the same volume as the given particle in the form of the particulate glass filler (iii-1) to the surface area of the particle in the form of the particulate glass filler (iii-1).

Preferably, the particulate glass filler (iii-1) is silanated, more preferably silanated with an organosilane as defined above.

The silanated glass flakes (iii-2) preferably have an average thickness between 50 nm and 1000 nm, and/or an average aspect ratio (long diameter/thickness) in the range of from 2:1 to 50:1. While the above described average thickness of the silanated glass flakes is from 50 to 1000 μm, the amount by weight of fractions of silanated glass flakes having different thickness may vary in a sample, wherein preferably, the silanated glass flakes include a fraction of silanated glass flakes having a thickness of 30 nm to 1500 nm, more preferably a thickness of 40 nm to 1000 nm, in an amount of at least 90% by weight.

Owing to the specific selection of average thickness and average aspect ratio of the silanized glass flakes (iii-2, excellent gloss and gloss retention can be obtained and ensured for a long period of time. According to the present invention, self-alignment of the silanized glass flakes (iii-2) within the polymer matrix of the cured dental composition is possible, whereby the glass flakes may arrange by partially overlapping. Planar and overlapping self alignment provides a smooth surface of the cured dental composition. Therefore, the dental composition will have an improved initial gloss compared to conventional composition containing glass in the form of spheres or fibers.

The term "gloss" as used herein means the optical property indicating how good or bad a surface reflects light in a specular direction. Gloss is affected by the refractive index of the material, the angle of incident light and the surface topography. Apparent gloss depends on the amount of specuar reflection, that is light reflected from the surface in an equal amount and the symmetrical angle to the one of incoming light. The specular reflection can be calculated by the Fresnel equation, which is well known in the field of optics. Surface roughness in micrometer range influences the specular reflection levels. A low intensity of specularly reflected light means the surface is rough and it scatters the light in other directions. Specifically, a totally nonreflective surface has zero gloss units (G.U.), while a perfect mirror would have 1000 G.U. at a measuring angle of 60°. Typically, for gloss measurement, a measuring angle of 60° is applied, since this angle is considered to be the best angle to use so as to provide the closest correlation to a visual observation. 10 G.U. or less means low gloss, 10 to 70 G.U. are considered as semigloss, and a gloss >70 G.U. is considered as high gloss. For dental restorations prepared from the cured dental composition according to the present invention, semigloss (10 to 70 G.U.) and high gloss (>70 G.U.) are preferred, wherein high gloss is particularly preferred.

The specific selection of the silanized glass flakes (iii-2 provides not only improved initial gloss, but also renders possible gloss retention for a relatively long period of time.

The term "gloss retention" as used herein means that the cured dental composition retains its initial gloss for a relatively long period of time, even when exposed to processing by a material removal method such as sanding or polishing, or likewise when the cured dental composition is exposed to typical daily loads such as tooth brushing, saliva fluid in the oral cavity and teeth grinding or clenching by the patient. It is readily understood that the planar, overlapping alignment of the glass flakes is more stable to the aforementioned loads, because in this arrangement, it is less likely that glass flake particles are removed by a mechanical load. That is, the surface of the cured dental composition will stay smooth for a relatively long time. Furthermore, regarding chemical resistance, for example in view of saliva fluid and/or acids from food, the planar, overlapping alignment of the glass flakes forms a kind of barrier which protects the cured dental composition as well as the tooth behind it from degradation by chemical influences such as acidity.

In addition, the silanated glass flakes (iii-2) may provide for an advantageous viscosity of the uncured dental composition. In particular, the silanated glass flakes (iii-2) may provide for a thixotropic behaviour of the dental composition.

According to the present invention, the combination of the particulate glass filler(s) (iii-1) and silanated glass flakes (iii-2) is suitable for adjusting the viscosity of the dental composition within a desired range. The silanated glass flakes (iii-2) may also be advantageous in terms of the mechanical properties and long-term mechanical resistance of the cured dental composition owing to the advantageous arrangement in the form of planar, overlapping alignment of the glass flakes, which arrangement may provide for uniform reinforcement and increased dimensional stability.

The combination of the silanated glass flakes (iii-2) and the particulate glass filer(s) (iii-1) is specifically selected in order to attain well balanced properties for the cured dental composition. Owing to the specific combination of silanated glass flakes (iii-2) and the particulate glass filler(s) (iii-1), excellent gloss, gloss retention and long-term chemical resistance may be attained as well as excellent mechanical properties and long-term mechanical resistance. The small, nano-sized silanated glass flakes (iii-2) readily arrange between and around the particulate glass filler(s) (iii-1) which may be considerable larger with up to 3 μm. Thereby, the small, nano-sized silanated glass flakes (iii-2) may self-align in the form of the above described planar, overlapping alignment, which may provide for a kind of barrier or shield effect. That is, the large particulate glass filler(s) (iii-1) particles are prevented from being removed from the cured dental composition by mechanical forces or chemical influences, since they are shielded by the planar, overlapping alignment of the silanated glass flakes (iii-2). As a result of this shielding, instead of a large particulate glass filler(s) (iii-1), at best, if that, the small, nano-sized silanated glass flakes (iii-2) are removed from the cured dental composition. Owing to this shield effect, an excellent gloss retention is attained, since after removal of a small particle, the surface of the cured dental composition will still be smooth and have an excellent gloss compared to a cured composition from which a large particle is removed, which results in a significantly irregular surface having a significantly deteriorated gloss. Furthermore, it is feasible that the above described shielding effect also provides for both a good mechanical and chemical resistance, since the shielding effects prevents aggressive chemical influences, such as acidic fluids, to infiltrate the large particle, which infiltration may result in removal of the particle when a mechanical force is applied, whereby gloss and long-term mechanical resistance is deteriorated.

It is easily understood that when the particulate glass filler(s) (iii-1) would be smaller than the glass flakes (iii-2), as taught for example in US 2006/0241205 A1, it is unlikely that the above described shielding effect is attained. Because, glass flakes being larger than the a structural filler in the form of e.g. a (spherical) glass filler particles may not readily arrange between and around the (spherical) glass filler particles, but rather, separate layers of (spherical) glass filler particles and glass flakes may form, since the large glass flakes may not be able to arrange in a planar, overlapping alignment between the small (spherical) glass filler particles. However, in case a layer of large glass flakes covers the (spherical) glass filler particles, the large glass flakes may be easily removed from the surface of the cured dental composition by mechanical forces or chemical influences. Then, the deterioration of gloss as well as chemical and mechanical resistance will be significantly higher compared to the dental composition according to the invention.

Preferably, the particulate glass filler(s) (iii-1) has/have an average particle size of from 0.3 to 2, more preferably of from 0.4 to 1.2.

For silanated glass flakes (iii-2), it is preferred that they have an average thickness between 80 nm and 1000 nm.

Most preferably, the particulate glass filler(s) (iii-1) has/have an average particle size of from 0.4 to 1.2, and the silanated glass flakes (iii-2) have (a) an average thickness between 50 nm and 1000 nm, and (b) an average aspect ratio (long diameter:thickness) in the range of from 2:1 to 50:1.

The glass of the silanated glass flakes (iii-2) preferably comprises the following components as oxides in percent by weight:

$SiO_2$=64-70
$B_2O_3$=2-5
$ZnO$=1-5
$Na_2O$=8-13
$MgO$=1-4
$CaO$=3-7
$Al_2O_3$=3-6, and up to 3 percent of $K_2O$ and $Ti_2$.

The glass of the silanated glass flakes (iii-2) is preferably an inert glass, wherein the term "inert glass" has the same meaning as described above for the particulate glass filler(s) (iii-1).

The silanated glass flakes (iii-2) are preferably obtainable by milling glass flakes having an aspect ratio of at least 20:1, and subsequently silanating the milled glass flakes. The milling of the glass flakes is not particularly limited and may be carried out with any apparatus typically applied for milling dental filler materials, such as a ball milling apparatus.

The thus obtained milled glass flakes may be silanated with a silane having one or more polymerizable groups reactive with the polymerizable compounds (ii). Silanes for silanating filler materials of dental compositions are well known and a large variety thereof for dental applications is described for example by J. M. Antonucci, Journal of Research of the National Institute of Standards and Technology, 2005, vol. 110, no. 5, pages 541 to 558.

The silanated glass flakes (iii-2) preferably have a particle size distribution determined by light scattering, wherein at least 70 percent, more preferably at least 75 percent, even more preferably at least 80 percent of the particles have a particle size of less than 50 µm.

It is preferred that the silanated glass flakes (iii-2) have a refractive index in the range of 1.46 to 1.60.

The particulate glass filler(s) (iii-1) and the silanated glass flakes (iii-2) may be suitably selected, preferably by selecting a ratio of the average particle size of the particulate glass filler(s) (iii-1) and the average thickness of the silanated glass flakes (iii-2) within the range of 10:1 to 1:1, more preferably 7:1 to 1.2:1, most preferably 4:1 to 1.4:1.

Preferably, the dental composition contains the silanated glass flakes (iii-2) in an amount of from 0.5 to 40 percent, more preferably 1 to 30 percent, even more preferably 3 to 20 percent by weight based on the total weight of the composition.

In the dental composition, the ratio of the weight of particulate glass filler(s) (iii-1) and the weight of the silanated glass flakes (iii-2) is preferably in the range of from 80:1 to 0.5:1, more preferably 40:1 to 1:1, even more preferably 20:1 to 1.5:1, yet even more preferably 10:1 to 2:1 and most preferably 5:1 to 2.5:1.

It is preferred that the dental composition according to the present invention is a resin modified dental cement composition.

The term "resin modified dental cement composition" means a glass ionomer composition containing reactive glass which reacts in an acid/base reaction, and further containing a water-soluble, polymerizable resin component. Typically, the water-soluble, polymerizable resin component is a polymer comprising units from polyalkenoic acids, preferably (meth)acrylic acids and derivatives thereof. Preferably, the water-soluble, polymerizable resin component has side chains having one or more polymerizable groups, which typically can be cured by means of light curing in the presence of a photo initiator and/or by a redox initiator system.

More preferably, the dental composition according to the present invention is a resin modified dental cement composition comprising one or more of the above described radically polymerizable polyacidic polymer(s) having repeating units of formula (I).

Most preferably, the dental composition is an aqueous resin modified dental cement composition comprising:
(i) a radically polymerizable compound in the form of:
  (i-1) the radically polymerizable polyacidic polymer having repeating units of formula (I),
  (i-2) optionally a hydrolysis-stable, water-soluble monomer having one radically polymerizable double bond and optionally a carboxylic acid group; preferably, the monomer has a molecular weight of at most 200 Da;

(i-3) optionally a hydrolysis-stable, water-soluble monomer having two or more radically polymerizable double bond(s) and optionally a carboxylic acid group (ii) a redox initiator system as described above, and (iii) a dental filler selected from a reactive particulate glass filler as described above.

The radically polymerizable polyacidic polymer according to (i-1) must be sufficient in number or percent by weight of hydroxyl groups and optional carboxylic acid groups to bring about the setting or curing reaction in the presence of the particulate glass filler according to (iii). Preferably, the radically polymerizable polyacidic polymer according to (i-1) is present in the aqueous resin modified dental cement composition in an amount of from 5 to 80 percent by weight, more preferably 10 to 50 percent by weight, still more preferably 15 to 40 percent by weight, based on the total weight of the composition.

According to (iii), the particulate glass filler comprises or consists of a reactive particulate glass filler as described above.

The particulate glass filler may be surface modified by a component according to (i-1), (i-2), (i-3) and/or (ii). In particular, the reactive particulate glass may be surface modified by one or more components of the redox initiator system (ii) in order to avoid contact of the one or more components of the polymerization initiator system (ii) with an acid under aqueous conditions.

The reactive particulate glass may alternatively or additionally be surface modified by a surface modifying agent. Preferably, the surface modifying agent is a silane as defined above. A silane provides a suitable hydrophobicity to the reactive particulate glass, which allows for an advantageous, homogeneous admixture with the organic components according to (i-1), (i-2), (i-3) and (ii) of the aqueous resin modified dental cement composition.

According to (i-2), the monomer having one radically polymerizable double bond is hydrolysis-stable and water-soluble. The aqueous resin modified dental cement composition may contain one or more monomer(s) according to (i-2).

According to (i-3), the monomer having one radically polymerizable double bond is hydrolysis-stable and water-soluble. The aqueous resin modified dental cement composition may contain one or more monomer(s) according to (i-3).

The term "hydrolysis-stable" used in connection with the radically polymerizable polyacidic polymer according to (1-1) and the monomers according to (i-2) and (i-3) means that these compounds are stable to hydrolysis in an acidic medium, such as in a dental composition. In particular, the compounds according to (i), (i-2) and (i-3) do not contain groups which hydrolyze in aqueous media at pH 2.5 at a temperature of 50° C. within one month, such as ester groups.

The term "polymerizable double bond" as used herein in connection with the monomer according to (i-2) and (i-3) means any double bond capable of addition polymerization, in particular free radical polymerization, preferably a radically polymerizable carbon-carbon double bond.

Further, the term "water-soluble" used in this connection means that at least 0.1 g, preferably 0.5 g of the monomer according to (i-2) or (i-3) dissolves in 100 g of water at 20° C.

The hydrolysis-stable, water-soluble monomers according to (i-2) and (i-3) are useful optional components of the aqueous resin modified dental cement composition, since the monomers according to (i-2) and (i-3) polymerize with the polymerizable polymer according to (i-1) in the presence of the polymerization initiator system according to (ii). Thereby, the monomers according to (i-2) and (i-3) may polymerize with itself and/or with the polymerizable pendant groups of the polymerizable compound according to (i-1). Hence, besides of the formation of a polymer formed of the monomer according to (i-2) and/or (i-3), there is a graft polymerization wherein monomer(s) according to (i-2) and/or (i-3) react with the polymerizable pendant groups $R^1$ of the polymerizable compound according to (i-1), whereby a graft polymer is formed. Furthermore, the graft side chains formed of the monomers according to (i-2) and/or (i-3) may additionally react with the pendant polymerizable groups of another polymerizable polymer according to (i-1), whereby a crosslinked polymer may be obtained.

In the following scheme, graft polymerisation by means of the monomer according to (i-2) is depicted byway of example for the repeating unit of formula (I) of the radically polymerizable polyacidic polymer according to (i-1), wherein acrylic acid is merely exemplary selected as a monomer according to (i-2). The letters "n" and "m" denote an integer of at least 1.

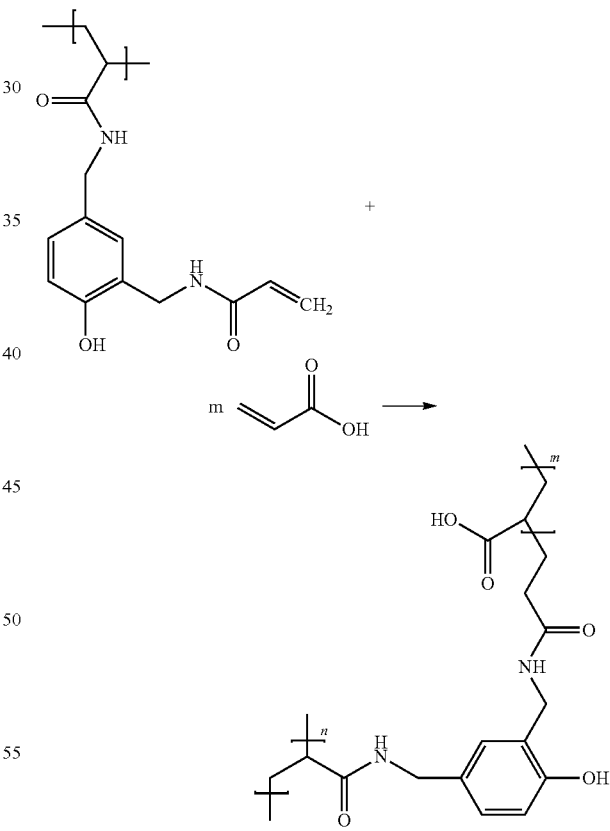

According to the present invention, one or a mixture of two or more monomers according to (i-2) and/or (i-3) may be used as component (i-2) and/or (i-3). A suitable monomer according to (i-2) or (i-3) is hydrolysis-stable. Specifically, a monomer according to (i-2) or (i-3) does not contain groups hydrolysing at pH 2.5 within one month at a temperature of 50° C. In particular, a suitable monomer according to (i-2) or (i-3) does not contain any ester group.

Furthermore, a suitable monomer according to (i-2) contains one radically polymerizable double bond. A suitable monomer according to (i-3) contains two or more radically polymerizable double bonds. Suitable radically polymerizable double bonds are carbon-carbon double bonds. In addition, the monomer according to (i-2) or (i-3) may contain a carboxylic acid group.

In a preferred embodiment, the monomer according to (i-2) is a compound represented by the following formula (XV):

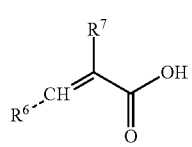

In formula (XV), $R^6$ is a hydrogen atom or a straight chain or branched $C_{1-3}$ alkyl group, and $R^7$ is a hydrogen atom or a straight-chain or branched $C_{1-6}$ alkyl group which may be substituted by a —COOH group. In formula (XV), the dotted line indicates that $R^6$ may be in either the cis or trans orientation. Preferably, $R^6$ is a hydrogen atom, and $R^7$ is a hydrogen atom or a $C_{1-3}$ alkyl group optionally substituted with a —COOH group. More preferably, $R^6$ is a hydrogen atom, and R is a hydrogen atom or a methyl group substituted with a —COOH group, that is compound of formula (XV) is acrylic acid or itaconic acid. Most preferably, the compound of formula (XV) is acrylic acid.

Preferably, in formula (XV), residues $R^6$ and $R^7$ are selected with the proviso that the molecular weight of the monomer having one radically polymerizable double bond according to (i-2) is at most 200 Da, more preferably at most 150 Da, most preferably at most 100 Da.

Furthermore, the hydrolysis-stable, water-soluble monomer having one radically polymerizable double bond may be 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide. 2-Hydroxyethyl methacrylate (HEMA) and hydroxypropyl methacrylate may also be used in certain embodiments.

The monomer according to (i-3) preferably is a compound selected from bisacrylamide, bisallylacrylamide, and biscycloalkylacrylamide compound, more preferably a compound of formula (E) described above.

The monomer according to (i-2) or (i-3) is preferably selected in view of a good processability and applicability of the final aqueousresin modified dental cement composition, in particular in terms of viscosity. Therefore, the viscosity of the monomer according to (i-2) or (i-3) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

Monomers according to (i-2) or (i-3), comprising a carboxylic acid group are particularly advantageous, since such monomers introduce additional carboxylic acid groups into the acidic polymer in the aqueous resin modified dental cement composition, which can undergo a cement reaction resulting in a further improved setting or curing reaction in the presence of the reactive particulate glass according to (iii).

Preferably, the monomer according to (i-2) or (i-3) is contained in the aqueous resin modified dental cement composition in an amount of from 0.1 to 20, more preferably 1 to 15 even more preferably 2 to 10 percent by weight based on the total weight of the aqueous resin modified dental cement composition. When the monomer according to (i-2) or (i-3) is absent, a long-term mechanical resistance may be low. On the other hand, when the amount of monomer according to (i-2) or (i-3) exceeds 20 percent of weight, shrinkage of the a set dental glass cement obtained from the present aqueous resin modified dental cement composition may occur.

It is preferred that for the dental composition according to the present invention, an elastomer optionally dissolved in a polymerizable acrylic monomer is excluded. More preferably, for the dental composition according to the present invention, an elastomer is excluded which is selected from a chlorosuphonated polyethylene, a chlorosulphonated copolymer of ethylene with minor amounts of propylene or of other olefins having 4 to 10 carbon atoms, or mixtures of sulphonyl chloride with chlorinated polyethylene. Such elastomers do not represent suitable components for dental compositions, but are typically applied in multicomponent adhesive compositions for industrial purposes, such as aerospace and automotive sectors, as disclosed for example in EP 0 511 635 A1.

Use of the Redox Initiator System and Container for Storing the Dental Composition The redox initiator system comprising (a) one or more clathrate compounds comprising a host molecule and one or more guest molecules, wherein the host molecule is selected from cyclodextrines, crown ethers, cucurbituriles and calixarenes, and the one or more guest molecules are reducing agents; and (b) an oxidizing agent, may be used in a dental composition, in particular in a dental composition as described above.

Besides, the above described dental composition may be comprised in a container for storing a dental composition.

Preferably, the container for storing a dental composition is adapted to be used in a mixing capsule device for dispensing the dental composition. For example, the mixing capsule device comprises two or more physically separate compartments, wherein in eachcompartment, a container containing a pack of the multi-part dental composition as described above may be inserted.

Hereinafter, the present invention will be described in further detail with the reference to examples. The present invention is not limited to the examples described below.

Definitions and Abbreviations

[Curing Time]
Working time: Period of time, measured from the start of mixing the powder and glass in the shown P/L ratio, during which it is possible to manipulate the material without an adverse effect on the properties.

Setting time: Point of time at which the mixture stopped being deformed even under pressing.

[Flexural Strength/E-Modulus]

The obtained dental glass ionomer compositions of Example 1 and Comparative Example 1-3 were filled in a stainless steel mould having the size (25±2) mm×(2.0±0.1) mm×(2.0±0.1) mm, for the preparation of test specimens. The thus obtained dental glass ionomer compositions were cured with a dental curing light (light-cured, LC) as well as without external power source (self-cured, SC). For the resulting cured dental glass ionomer composition, the flexural strength has been determined according to ISO 4049.

[Abbreviations]

tBDA: 4-tert-Butyl-N,N-dimethylaniline tBDAC: 4-tert-Butyl-N,N-dimethylaniline/β-Cyclodextrine clathrates tBDA-HCl: 4-tert-Butyl-N,N-dimethylaniline hydrochloride tBDA-Mal: 4-tert-Butyl-N,N-dimethylaniline maleinate NapTS: Sodium-p-toluene sulfinate KPS: Pottasium persulfate CQ: Camphorquinone Examples Synthesis Example 1:

Synthesis of 4-tert-Butyl-N,N-dimethylaniline/β-Cyclodextrin clathrates (tBDAC)

200 g (0.176 mol) of β-Cyclodextrin were dissolved in 12000 mL of water. The slurry was stirred rapidly until the β-Cyclodextrin dissolved. After that, 48.86 g (0.264 mol, 1.5 fold excess) of 4-tert-Butyl-N,N-dimethylaniline (tBDA) were added to the solution. Formation of a milky white precipitate was observed shortly after addition of tBDA. The resulting mixture was stirred rapidly for 48 hours. The precipitate was collected by filtration using a glass fit, washed with 2000 mL water and subsequently with 2000 mL acetone. After drying in a vacuum oven at 37° C. for 48 h, the product was sieved through a net with a mesh size of 180 µm. The obtained $^1$H NMR indicated a 1:1 complex between tBDA and β-Cyclodextrin (refer to FIG. 1). The tBDA-clathrate was yielded in an amount of 208 g (~90% theoretical yield). 200 g (0.176 mot) of β-CD were dissolved in 8000 mL of water. The solution was stirred rapidly and heated until the β-CD dissolved. After cooling to room temperature, 40.22 g (0.264 mot) of cumene hydroperoxide (CHP) were added to the solution. The resulting solution was stirred rapidly for about 20 hours. Formation of a milky white precipitate was observed. The precipitate was collected by filtration, washed with methyl tert-butyi ether and dried under high vacuum. The stoichiometry of the complex formed was determined from the ratio of the peak areas for the aromatic protons of the CHP and the H-1 glucoside protons of the β-CD. The complex was yielded in an amount of 180 g (0.14 mol, yield 80%). The obtained $^1$H-NMR indicated a 1:1 complex between CHP and β-CD.

Synthesis Example 2

Synthesis of 4-tert-Butyl-N,N-dimethylaniline maleinate (tBDA-Mal)

5.0 g (28.2 mmol) $t^{BDA}$ were solved in 50 ml 2-propanol at room temperature. Under stirring 4.3 g (36.7 mmol) maleic acid were added. The mixture was stirred overnight. A suspension was formed and the solid was filtered off. The white solid was dried under vacuum at room temperature.

1HNMR [ppm] in DMSO: 7.23 and 7.25 (2H, d; Ha, Ha'); 6.76 and 6.79 (2H, d; Hb, Hb'); 6.25 (2H, s; 2xHc); 2.88 (6H, s; 2xNMe); 1.24 (9H, s; t-Bu)

Melting point: 130° C.

tBDA Maleic acid:

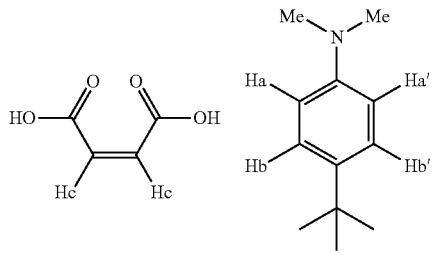

Synthesis Example 3

Synthesis of 4-tert-Butyl-N,N-dimethylaniline hydrochloride (tBDA-HC)

3.2 g tBDA were solved in 50 mL 2-propanol at room temperature. Under stirring 5.7 mL 4 molar HCl solution in dioxane (22.9 mmol HCl) were added. The mixture was stirred over weekend. A suspension was formed and the solid was filtered off. The white solid was dried under vacuum at room temperature.

1HNMR [ppm] in DMSO: 7.71 and 7.69 (2H, d; Ha, Ha'); 7.57 and 7.55 (2H, d; Hb, Hb'); 3.09 (6H, s; 2xNMe); 1.29 (9H, s; t-Bu)

Melting point: 215° C.

Application Example 1 and Comparative Example 1-3

Composition

Aqueous dental glass ionomer compositions of Example 1 according to the invention and of the Comparative Examples 1-3 have been prepared by forming a liquid and a powder composition of the ingredients listed in Table 1 below, which respectively add up to 100 wt %, and admixing both parts in the shown powderliquid (P/L) ratio.

TABLE 1

Aqueous dental glass ionomer compositions of Example 1 and of the Comparative Examples 1-3.

|  |  | Example 1 | Comparative Example 1 | Comparative Example 2 | Comparative Example 3 |
|---|---|---|---|---|---|
| Liquid | Water | 34.10 | 34.10 | 34.10 | 34.23 |
|  | Cross-linker | 15.00 | 15.00 | 15.00 | 15.00 |
|  | Modified polyacid | 25.00 | 25.00 | 25.00 | 25.00 |
|  | Acrylic acid | 25.25 | 25.25 | 25.25 | 24.39 |
|  | tBDA | 0 | 0 | 0 | 1.73 |
|  | CQ | 0.62 | 0.62 | 0.62 | 0.62 |
|  | Inhibtitor | 0.03 | 0.03 | 0.03 | 0.03 |
|  | Σ | 100 | 100 | 100 | 100 |
| Powder | Reactive glass mixture | 94.70 | 98.64 | 98.38 | 99.34 |
|  | tBDAC | 4.64 | 0 | 0 | 0 |
|  | tBDA-HCl | 0 | 0.70 | 0 | 0 |

TABLE 1-continued

Aqueous dental glass ionomer compositions of Example 1 and of the Comparative Examples 1-3.

|  | Example 1 | Comparative Example 1 | Comparative Example 2 | Comparative Example 3 |
|---|---|---|---|---|
| tBDA-Mal | 0 | 0 | 0.96 | 0 |
| NapTS | 0.44 | 0.44 | 0.44 | 0.44 |
| KPS | 0.22 | 0.22 | 0.22 | 0.22 |
| Σ | 100 | 100 | 100 | 100 |
| P/L ratio | 3.0 | 3.0 | 3.0 | 3.0 |

Results:
Working Time, Setting Time, Flexural Strength and e-Modulus

|  |  | Example 1 |  | Comparative Example 1 |  | Comparative Example 2 |  | Comparative Example 3 |  |
|---|---|---|---|---|---|---|---|---|---|
| Curing time | Working time (seconds) | 180 | PRO01-159-02 F | 180 | MTO08-64-02 | 180 | MTO08-64-02 | 150 | SAH01-144-01 B |
|  | Setting time (seconds) | 240 | PRO01-159-01 F | 203 | PRO01-103-03 A | 270 | PRO01-120-01 E | n.n. |  |
| Flexural strength (SC) [MPa] |  | 93 ± 7 | MSO06-164-01 B | 90 ± 13 | SKA17-104-01 | 96 ± 16 | SKA17-103-02 A | 95 ± 8 | SAH01-147-01 A |
| Flexural strength (LC) [MPa] |  | 98 ± 8 | SKA17-133-02 A | 115 ± 4 | SKA17-105-02 B | 111 ± 6 | SKA17-104-02 | 119 ± 15 | SAH01-143-02 A |
| E-Modulus (SC) [MPa] |  | 10460 ± 280 | MSO06-164-01 B | 10820 ± 320 | SKA17-104-01 | 10730 ± 750 | SKA17-103-02 A | 11600 ± 230 | SAH01-147-01 A |
| E-Modulus (LC) [MPa] |  | 10000 ± 1330 | SKA17-133-02 A | 10820 ± 320 | SKA17-105-02 B | 11550 ± 370 | SKA17-104-02 | 12590 ± 760 | SAH01-143-02 A |

Figure 2:
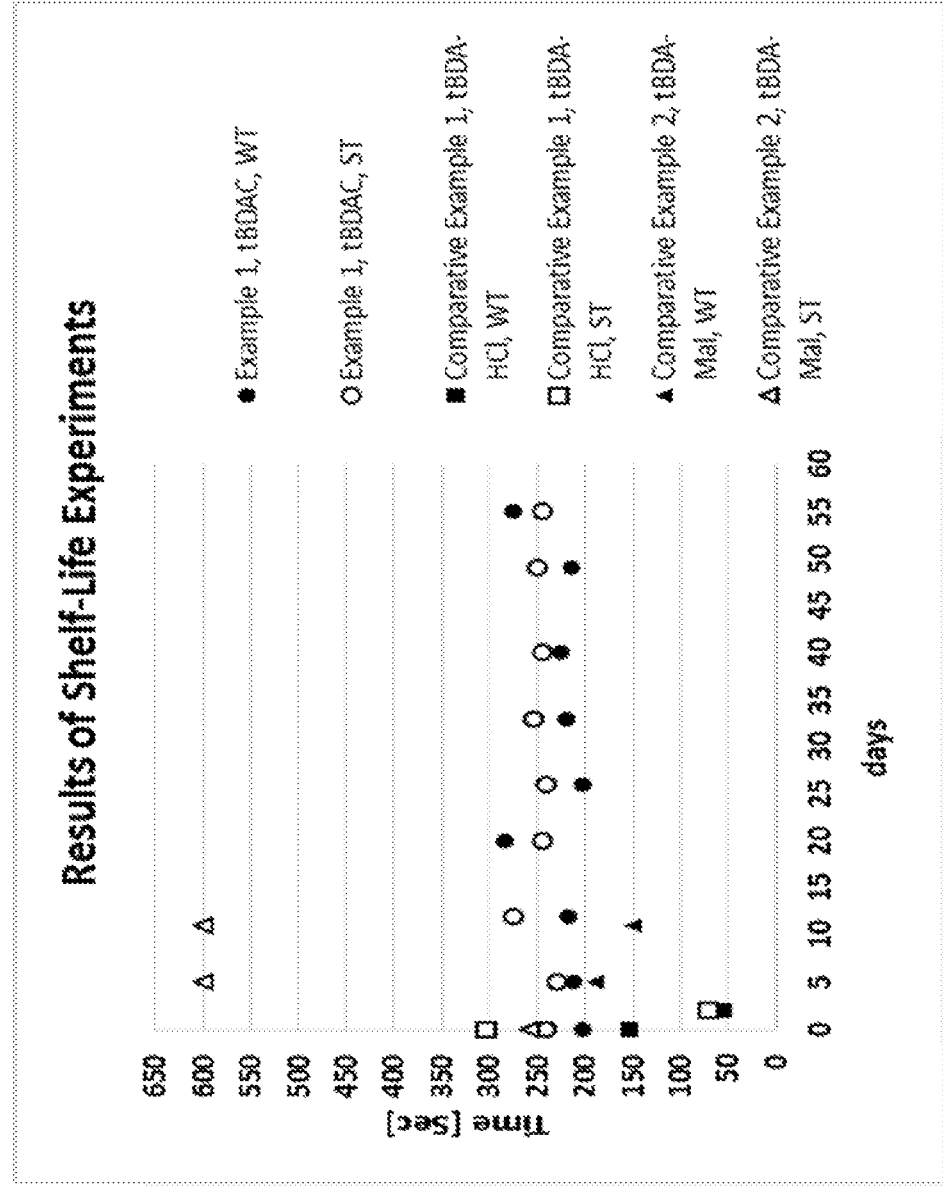
FIG. 2 shows results of the Shelf-Life Experiments for Example 1 and Comparative Example 1-2.

Shelf-Life:

In order to evaluate the preliminary shelf-life of the material, the powder part, which comprises the redox active compounds was stored at 50° C. up to 56 days (2 month). The working- and setting time of Application example 1 and of the Comparative Examples 1-2, was measured in suitable intervals. Only Example 1, comprising the host-guest complex between tBDA and β-Cyclodextrin (tBDAC) showed a sufficient shelf-life for 2 month at 50° C. In contrast Comparative Example 1 and 2 were not functional after 2-/11 days stored at mentioned conditions resulting in highly decreased-/increased curing kinetics (FIG. 2).

The invention claimed is:

1. A dental composition comprising
  (i) a radically polymerizable compound; and
  (ii) a redox initiator system comprising
    (a) one or more clathrate compounds comprising
      (a1) a host molecule and
      (a2) one or more guest molecules,
    wherein the host molecule is selected from crown ethers, cucurbiturils, and calixarenes, and the one or more guest molecules are reducing agents; and
    (b) an oxidizing agent.

2. The dental composition according to claim 1, wherein the reducing agent is an aromatic tertiary amine, a phosphine or a borane.

3. The dental composition according to claim 1, wherein the reducing agent is a tertiary amine of the following formula (I):

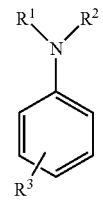

(I)

wherein $R^1$ and $R^2$ which may be the same or different, independently represent straight chain, branched or cyclic $C_{1-8}$ alkyl group, or $R^1$ and $R^2$ form together with the nitrogen atom to which they are bonded a 3-8 membered saturated heterocyclic ring; and $R^3$ represents an organic group.

4. The dental composition according to claim 3, wherein the reducing agent is 4-tert.-butyl-N,N-dimethylaniline.

5. The dental composition according to claim 1, wherein the molar ratio of the guest molecules: the host molecules is in the range of from 1:0.5 to 1:3.

6. The dental composition according to claim 1, wherein the oxidizing agent is a peroxide which is selected from cumyl hydroperoxide, tert-butyl peroxybenzoate, tert-butylperoxy (2-ethylhexyl)carbonate, tert-butylhydroperoxide, di(tert-butyl)peroxide, tert-butylperoxy-3,5,5-trimethyl-hexanoate, and potassium peroxydisulfate.

7. The dental composition according to claim 1, which is a resin modified dental cement composition.

8. The dental composition according to claim 1, which is a two-pack dental composition.

9. The dental composition according to claim 1, wherein the redox initiator system including the one or more clathrate compounds and the oxidizing agent are stored as a mixture in a single pack.

10. A dental composition comprising
  (i) a radically polymerizable compound; and
  (ii) a redox initiator system comprising
    (a) one or more clathrate compounds comprising
      (a1) a host molecule and
      (a2) one or more guest molecules, wherein the host molecule is selected from cyclodextrins, crown ethers, cucurbiturils, and calixarenes, and the one or more guest molecules are borane reducing agents; and (b) an oxidizing agent.

11. The dental composition of claim 10, wherein the borane has a structure of the following formula (II):

$$R^{12}R^{13}R^{14}B \quad (II)$$

wherein $R^{12}$, $R^{13}$, and $R^{14}$ which may be the same or different, independently represent a $C_{1-8}$ alkyl group or a $C_{4-10}$ aryl or heteroaryl group.

* * * * *